United States Patent
Livneh et al.

(10) Patent No.: US 11,753,453 B2
(45) Date of Patent: Sep. 12, 2023

(54) PEPTIDE KINASE INHIBITORS AND METHODS OF USE THEREOF

(71) Applicant: B.G. NEGEV TECHNOLOGIES AND APPLICATIONS LTD., Beer-Sheva (IL)

(72) Inventors: Etta Livneh, Rehovot (IL); Sigal Frost, Kibbutz Nir-Yizhak (IL); Esti Yeger-Lotem, Omer (IL); Ilan Smoly, Tel Aviv (IL); Assaf Ben Ari, Tel Aviv (IL)

( * ) Notice: Subject to any disclaimer, the term of this patent is extended or adjusted under 35 U.S.C. 154(b) by 0 days.

(21) Appl. No.: 17/394,431

(22) Filed: Aug. 5, 2021

(65) Prior Publication Data

US 2021/0371482 A1    Dec. 2, 2021

Related U.S. Application Data

(63) Continuation of application No. 16/486,832, filed as application No. PCT/IL2018/050182 on Feb. 19, 2018, now abandoned.

(60) Provisional application No. 62/460,810, filed on Feb. 19, 2017.

(51) Int. Cl.
| | | |
|---|---|---|
| *C07K 14/47* | (2006.01) | |
| *A61P 35/00* | (2006.01) | |
| *A61K 45/06* | (2006.01) | |
| *A61K 38/00* | (2006.01) | |

(52) U.S. Cl.
CPC .......... *C07K 14/4703* (2013.01); *A61K 45/06* (2013.01); *A61P 35/00* (2018.01); *A61K 38/00* (2013.01)

(58) Field of Classification Search
CPC ..... C07K 14/4703; A61P 35/00; A61K 45/06; A61K 38/00
See application file for complete search history.

(56) References Cited

U.S. PATENT DOCUMENTS

| | | | |
|---|---|---|---|
| 2009/0075875 A1* | 3/2009 | Hoffman | A61P 7/00 436/501 |
| 2013/0296224 A1 | 11/2013 | Ben-Hamo et al. | |
| 2016/0003854 A1* | 1/2016 | Hughes | G01N 33/5041 435/254.11 |

FOREIGN PATENT DOCUMENTS

| | | | | |
|---|---|---|---|---|
| WO | WO 2015/188110 | * | 12/2015 | ............. A61K 47/48 |

OTHER PUBLICATIONS

Raveh-Amit et al., 2009, Translational Control of Protein Kinase C eta by Two Upstream Open Reading Frames, Molecular and Cellular Biology, 29(22): 6140-6148.*

(Continued)

*Primary Examiner* — Amber D Steele
(74) *Attorney, Agent, or Firm* — JMB Davis Ben-David

(57) ABSTRACT

Described herein are isolated regulatory peptides of protein kinase C, chimeric peptides thereof, and their variants. Use of the described peptides, in compositions and methods for treatment of cellular proliferation pathologies is also described.

14 Claims, 12 Drawing Sheets

Specification includes a Sequence Listing.

(56) References Cited

OTHER PUBLICATIONS

Lee et al., 2010, Lipo-oligoarginines as effective delivery vectors to promote cellular uptake, Mol Biosyst, 6(10): 2049-2055.*
Martin et al., 2005, PKCeta as a therapeutic target in glioblastoma multiforme, Expert Opinion on Therapeutic Targets, 9(2): 299-313.*
Deepanwita Pal et al., 2014, The unique protein kinase C eta: Implications for breast cancer (Review), International Journal of Oncology, 45: 493-498.*
Raveh-Amit, Hadas et al. Translational control of protein kinase Ceta by two upstream open reading frames. Molecular and cellular biology, 2009, 29.22: 6140-6148.
539604 PKCeta Pseudosubstrate Inhibitor. Myristoylated-Calbiochem. The PKCeta Pseudosubstrate Inhibitor, Myristoylated controls the biological activity of PKCeta. This small molecule/inhibitor is primarily used for Phosphorylation & Dephosphorylation applications. Product specification retrieved from Merck catalog. http://www.merckmillipore.com/INTL/en/product/PKC-Pseudosubtrate-Inhibitor-Myristoylated-Calbiochem. EMD_BIO-539604#_anchor_PDS, Jan. 11, 2010.
Harrington E O et al, "Endothelial Proliferation, Migration, and Differentiation Are Blunted by Conditionally Expressed Protein Kinase C Pseudosubstrate Peptides", Biochemical and Biophysical Research Communications, vol. 271, No. 2, pp. 499-508, 2000.
Sara Abu-Ghanem et al, "PKC[eta] expression contributes to the resistance of hodgkin's lymphoma cell lines to apoptosis", Cancer Biology & Therapy, (2007), vol. 6, No. 9, 1371-1376.
Cristina Barbosa et al, "Gene Expression Regulation by Upstream Open Reading Frames and Human Disease", PLOS Genetics, (2013), vol. 9, No. 8, doi:10.1371.
Deepanwita Pal et al, "The unique protein kinase C[eta]: Implications for breast cancer (Review)", International Journal of Oncology, GR, (2014), vol. 45, No. 2, pp. 493-498.
U Zurgil et al, "PKC[eta] promotes senescence induced by oxidative stress and chemotherapy", Cell Death & Disease, (Nov. 1, 2014), vol. 5, No. 11, doi:10.1038/cddis.2014.481, pp. e1531-e1531.
Database Geneseq [online] Jan. 31, 2013, "Triticum aesitvum derived polypeptide, SEQ ID 13377" retrieved from EBI accession No. GSP:BAI79241.
Zurgil et al., 2014 PKCeta is an anti-apoptotic kinase that predicts poor prognosis in breast and lung cancer, Biochem Soc Trans, 42: 1519-1523.
Patra et al. 2012. Chemically Modified Peptides TGargeting the PDZ Domain of GIPC as a therapeutic Approach for Cancer, ACS Cehm Biol, 7: 770-779.
Selbie et al. 1993, Molecular Cloning and Characterization of PKCtau, an Atypical Isoform of Protein Kinase C Derived from Insulin-sectreting Cells, The Journal of Biological Chemistry, 268(32): 24296-24302.
Methods in Molecular Biology, Cell-Penetrating Peptides, Langel (ed), 2015.

* cited by examiner

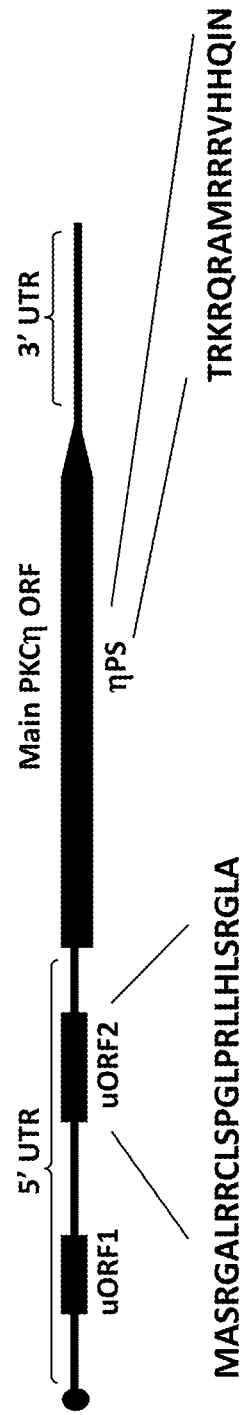

Fig. 1B

```
Human     MASRGALRRCLSPGLPRLLLHLSRGLA
Rhesus    MASRGALGRCLSPGLPRLLQLSRGLA
Elephant  MAGRGGLGRCFSPELPLLRLPRGLA
Dog       MTSGGGLGRCFSPELRRLPPRGLA
Mouse     MAGRRGLGRCFFPELPPRPWQRRGLP
Rat       MAGRRGLGCCFSRELPPRAWLRRGLP
```

Fig. 1C

```
              PKC α     RFARKGALRQKNVHEVKD
Conventional  PKC β     RFARKGALRQKNVHEVKN
              PKC γ     LFCRKGALRQRVVHEVKS
              PKC δ     TMNIRGAIRQAKIHYIKN
Novel         PKC ε     PRKRQGAVRRRVHQVN-
              PKC η     TRKRQRAMRRRVHQIN-
Atypical      PKC ζ     SIYRRGARRWQKLYRAN-
              PKC λ/ιL  HQRRGAIQAKVHVKC uORF2 -   MASRGALRRCLSPGLPR
```

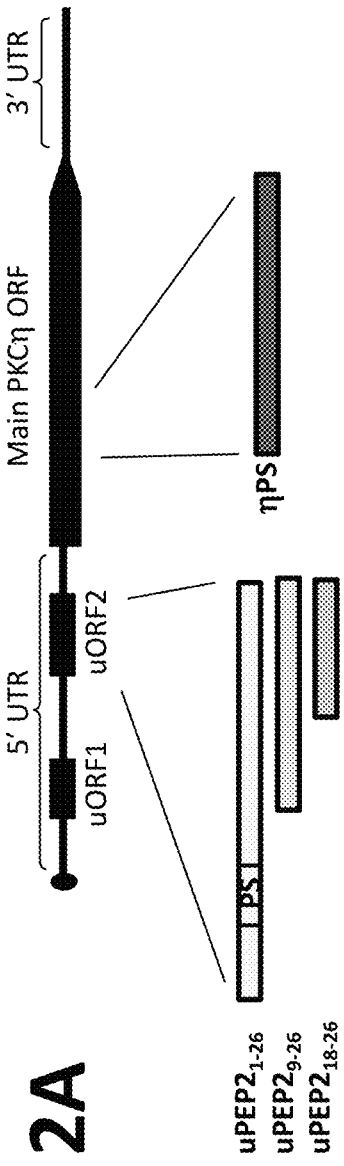
Fig. 2A
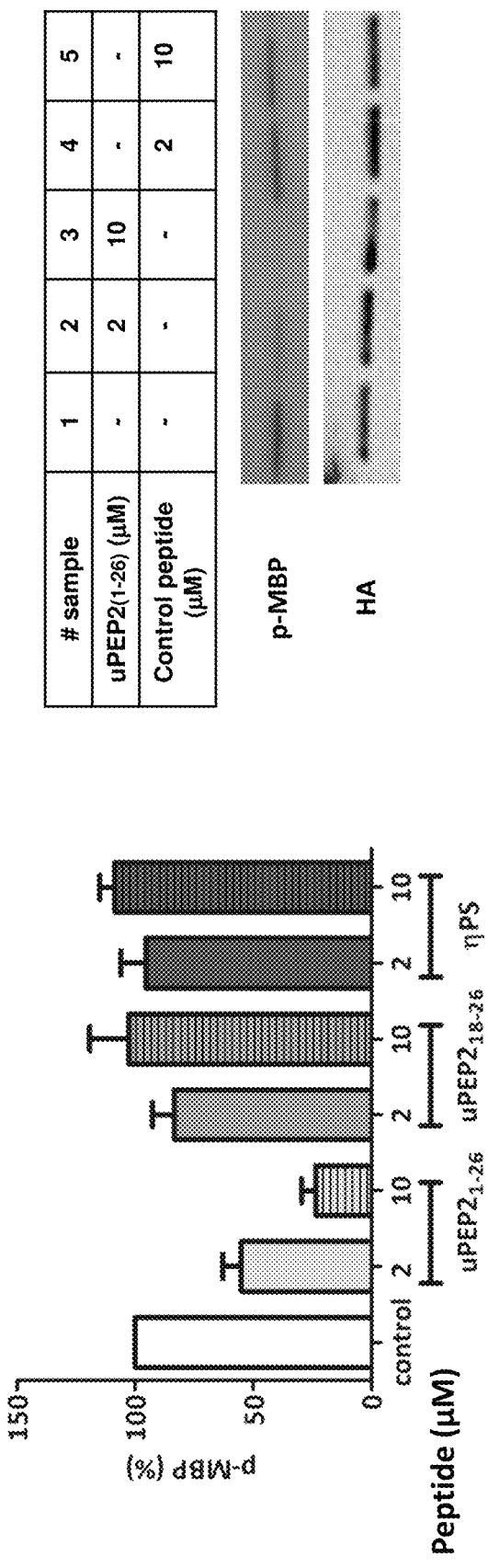
Fig. 2C
Fig. 2B

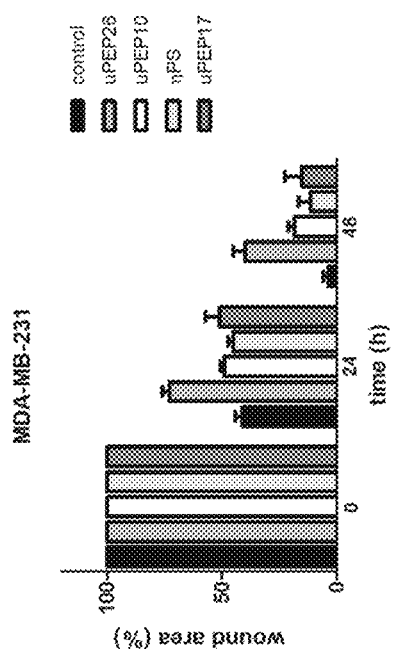
Fig. 3A
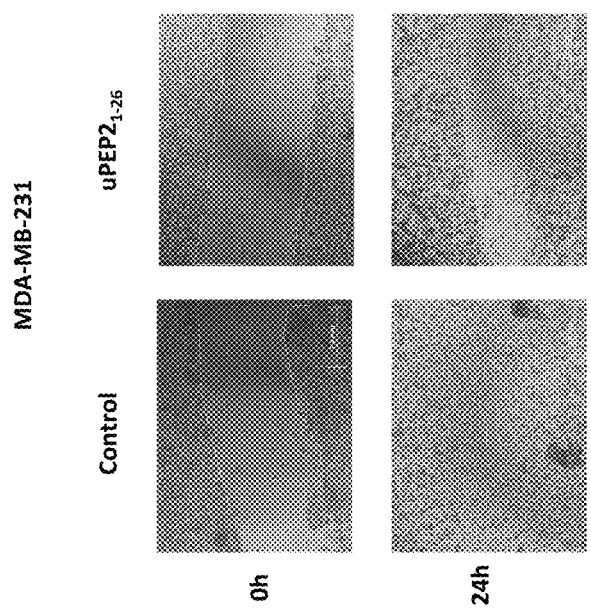
Fig. 3B
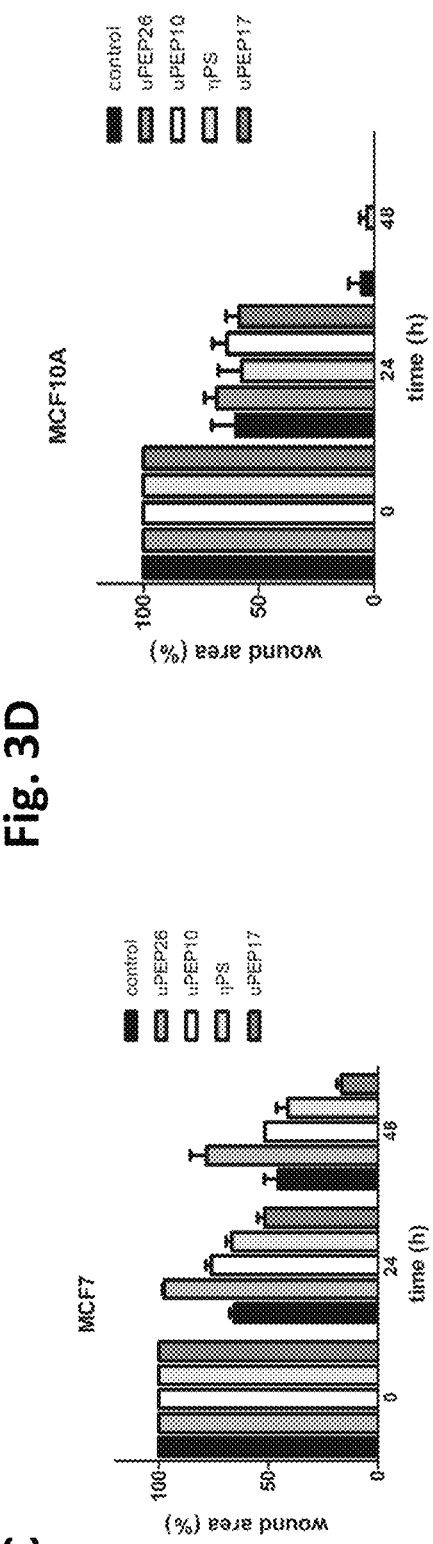
Fig. 3C
Fig. 3D

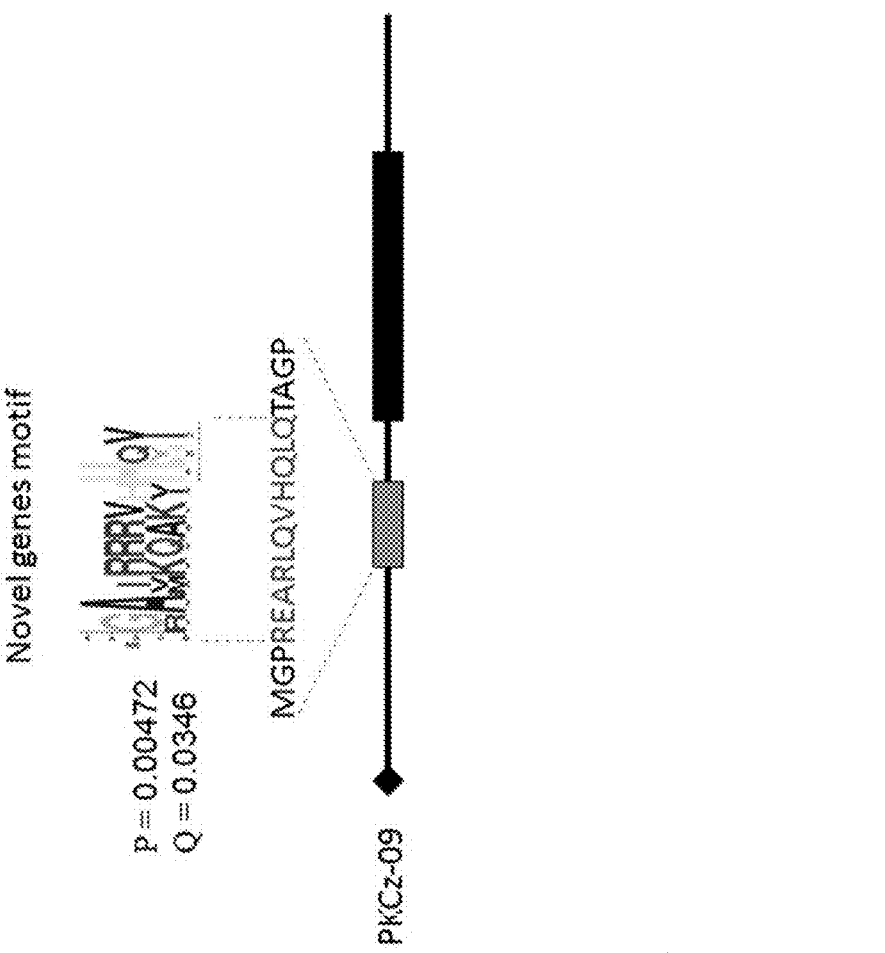
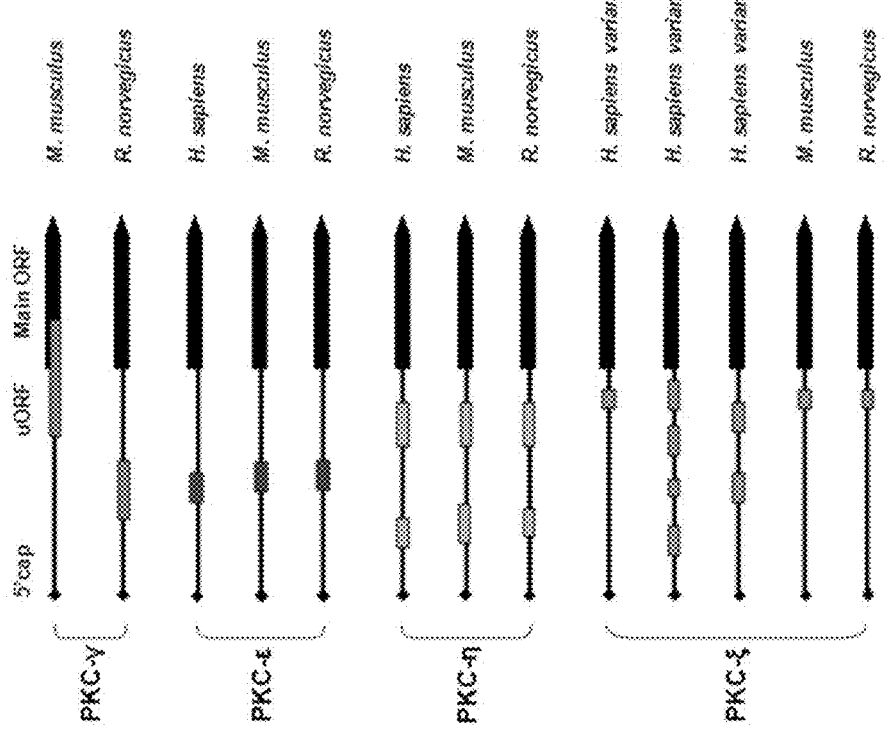

PEPTIDE KINASE INHIBITORS AND METHODS OF USE THEREOF

CROSS-REFERENCE TO RELATED APPLICATIONS

This is a Continuation of U.S. patent application Ser. No. 16/486,832, filed on Aug. 18, 2019, which is the US National Stage of International Patent Application No. PCT/IL2018/050182, filed Feb. 19, 2018; which in turn claims the benefit of U.S. Provisional Patent Application No. 62/460,810, filed Feb. 19, 2017. The contents of the foregoing patent applications are incorporated by reference herein in their entirety.

FIELD

This disclosure relates to isolated regulatory peptides of protein kinase C, uORF's, chimeric peptides thereof, and their variants. Use of the described peptides, in compositions and methods for treatment of cellular proliferation pathologies is also described.

BACKGROUND

Translational regulatory elements function in cells to rapidly change the protein expression landscape in response to internal or external stimuli. Among these elements are upstream open reading frames (uORFs) located at the 5'-untranslated region of mRNAs. Bioinformatics studies revealed the presence of uORFs in about 40% of human mRNAs. uORFs usually correlate with reduced protein expression levels since they decrease the efficiency of translation initiation of downstream ORF. Previously, we reported that the expression of the protein kinase C isoform PKCeta is regulated via two uORFs and showed their potential to be translated into short peptides.

Protein kinases, including the various PKC isoforms, are recognized for their role in regulation of myriad biological processes, and aberrant PKC expression is understood to be a factor in several pathologies including those involving cellular proliferation. Thus, a continuing need exists to regulate PKC expression.

SUMMARY

Described herein are isolated and synthetic, peptides derived from an uORF of the PKCeta isoform, and particularly an isolated polypeptide including an amino acid sequence at least 70% identical to the amino acid sequence set forth as SEQ ID NO: 32.

Further described herein, is the isolated polypeptide of SEQ ID NO: 32 wherein the amino acid at position 10 is alanine, as set forth herein as SEQ ID NO: 5. Additionally described herein, is the isolated polypeptide of SEQ ID NO:32 wherein the amino acid at position 10 is cysteine, as set forth herein as SEQ ID NO: 1.

Further described herein are combinations of synthetic peptides set forth herein as SEQ ID NOs: 1-9, and a chemotherapy agent for use in treatment of aberrant cell proliferation (e.g. cancer), such as in methods of treatment and use in the preparation of a medicament for treatment of cancer.

Additionally, described herein are isolated, synthetic, and chimeric peptides derived from an uORF of the PKCzeta isoform, and particularly an isolated polypeptide including an amino acid sequence at least 75% identical to the amino acid sequence set forth as SEQ ID NO: 11. Nucleic acids encoding the described peptides are also provided.

Further described herein are compositions including the described peptides and/or peptide-encoding nucleic acids for use in the treatment of a disease or condition associated with aberrant cell proliferation, including for use in the preparation of a medicament for treatment of the disease or condition.

Methods of using the described peptides and/or nucleic acids in treatments for a disease or condition associated with aberrant cell proliferation are also provided.

The foregoing and other objects, features, and advantages will become more apparent from the following detailed description, which proceeds with reference to the accompanying figures.

BRIEF DESCRIPTION OF THE DRAWINGS

FIGS. 1A-1C are schematic representations of the mRNA of human PKCη (PKCeta), its two uORFs and pseudosubstrate (PS) sequence, and their homologies with other PKCs of other species. FIG. 1A: The amino acids sequences uORF2 (SEQ ID NO: 1) and the pseudosubstrates (PS) sequence (SEQ ID NO: 19) of PKCη is depicted in one-letter code. FIG. 1B: The amino acids sequence of uORF2 shows high conservation. The amino acid sequence encoded by human uORF2 (SEQ ID NO: 1) was aligned with uORFs encoded by homologous PKCη in other mammalian species (SEQ ID NOs: 20-24, Rhesus, Elephant, Dog, and Rat, respectively). FIG. 1C: The amino acid sequence of the pseudosubstrate of PKCη (ηPS) (SEQ ID NO: 19) was aligned with PS sequences of all other human PKCs (SEQ ID NOs: 25-31, PKCα, PKCβ, PKCγ, PKCδ, PKCε, PKCζ and PKCλ/ι, respectively) and with the sequence encoded by uORF2 (SEQ ID NO: 3). All sequences are presented in a one-letter code; multiple sequence alignment was carried via the HHpred toolkit.

FIGS. 2A-2D show a schematic representation of peptides derived from PKCη and demonstrate the ability of the uORF2-encoded peptide (uPEP2$_{1\text{-}26}$) to inhibit PKCs kinase activity. FIG. 2A is a schematic view of the peptides derived from PKCη and used in the examples described herein. uPEP$_{1\text{-}26}$ refers to the complete peptide encoded by uORF2; uPEP$_{9\text{-}26}$ and uPEP$_{18\text{-}26}$ refer to control peptides, which lack the PS motif; ηPS refer to a peptide containing the internal PS domain of PKCη. FIG. 2B shows the results of testing the impact of different peptides on the kinase activity of PKCη. The kinase activity of PKCη was measured using Myelin Basic Protein (p-MBP) as a substrate and γ-$^{32}$P radioactive kinase assays. All values were normalized to the control sample without a peptide (Cont.). The data shown are the means of three separate experiments, and is also presented as the gel in FIG. 2C. FIG. 2D: Kinase assays were conducted as described in FIG. 2B, using uPEP$_{1\text{-}26}$ at 2 μM concentration are depicted. All values were normalized to the control sample (without peptide). The data shown are the means of three separate experiments.

FIGS. 3A-3D demonstrate the ability of the peptide encoded by uORF2 (uPEP2$_{1\text{-}26}$) to inhibit cell migration of breast cancer cells. FIG. 3A is a photograph taken from the scratch assay performed on MDA-MB-231 cells. Cells were seeded in 24-well plate and incubated for 4 hours with the indicated peptides in a free-serum media. After 4 hours, a scratch was made with a 200 μl pipette tip. Photographs of a selected area of each scratch were taken at indicated time points. Areas were measured by ImageJ software. FIGS. 3B-3D are graphs representing the analysis of the scratch assay performed as described in FIG. 4A on cell lines MDA-MB-231, MCF-7 and MCF10A, respectively. All values were normalized to time 0 of each well and presented in percentage.

FIG. 4A: MCF-7 cells were seeded onto 48-well plates. 24 hours later, the cells were incubated for 24 hours with the indicated peptides). Following incubation, the medium with tested peptide was gently aspirated from each well and 25 µL of PrestoBlue reagent was added to each well of the 48-well plate and incubated at 37° C. in 5% $CO_2$ for 15 min, as recommended. The absorbance was detected by 'Infinite M200 PRO' reader. FIGS. 4B-4D are the results of experiments identical to that described by FIG. 4A, but performed on cells lines U251 MG (glioblastoma cell line), MDA-MB-231 and MCF10A, respectively.

FIG. 6A: MCF-7 cells were seeded in 96 well plate and incubated for 24 hours with the indicated peptides. After 24 hours, the proliferation rate was monitored using XTT kit (Biological Industries, Israel) according to the manufacturer's instructions. FIG. 6B: MDA-MB-231 cell line were tested as indicated in FIG. 6A. FIG. 6C: HeLa cells were tested as indicated in FIG. 6A.)

FIG. 7A: 4T1 cells expressing shPKCη (SEQ ID NO: 33) or scrambled control were injected into mammary fat pad of 8-week-old female BALB/c mice. Tumor diameters were measured every week with vernier calipers. FIG. 7B: The mice were sacrificed after 8 weeks, and number of metastasis formed in the lungs was counted using Bouin's solutions. Error bars represent the mean±s.e.m, statistical analysis indicates for statistical significance in two-tailed, unpaired sample t-test.

FIGS. 8A-8B are schematic representations of the 5'UTRs of additional PKCs which contain uORFs and the PS motif. FIG. 8A: Bioinformatics revealed the presence of a uORF in PKCeta and PKCzeta. The 5' cap structure is shown as a diamond, the 5' UTR as a straight line, the CDS as a black arrow, and uORFs as boxes. uORFs were found by the ORF-finder software (NCBI). FIG. 8B: The amino acid sequence of the uORF of PKCzeta containing a PS motif is depicted (SEQ ID NO: 11).

BRIEF DESCRIPTION OF THE DESCRIBED SEQUENCES

Figure 2D:
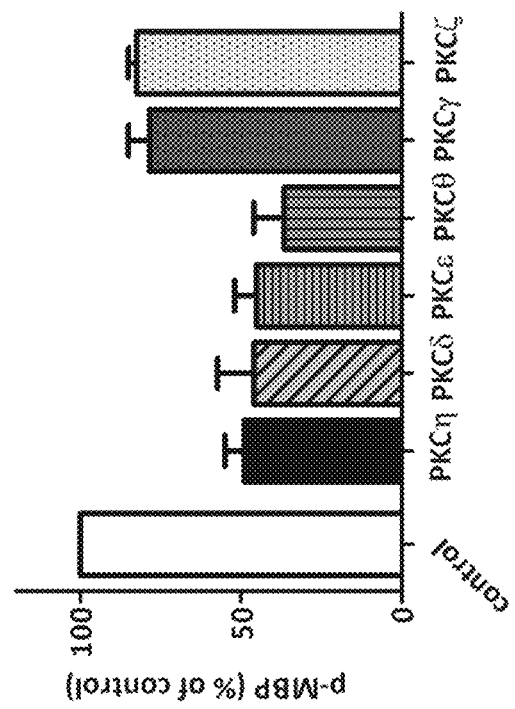
Figure 4A:
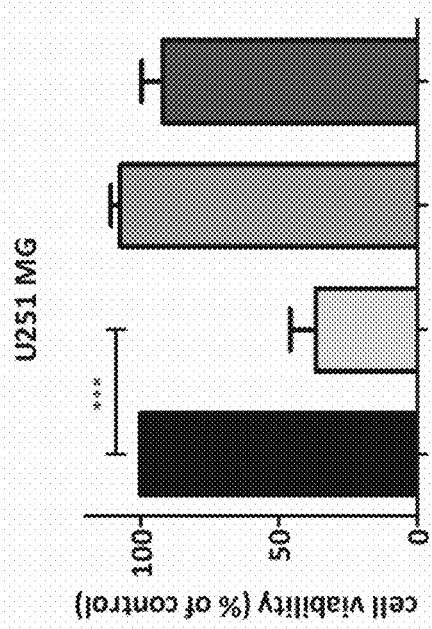
FIGS. 4A-4D show the ability of the peptide encoded by uORF2 (uPEP2$_{1-26}$) to reduce viability of breast cancer and glioblastoma cells.
Figure 4B:
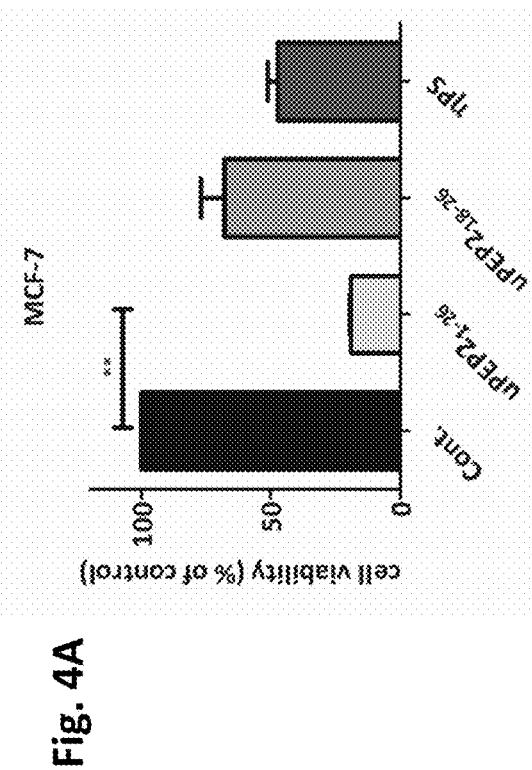
Figure 4C:
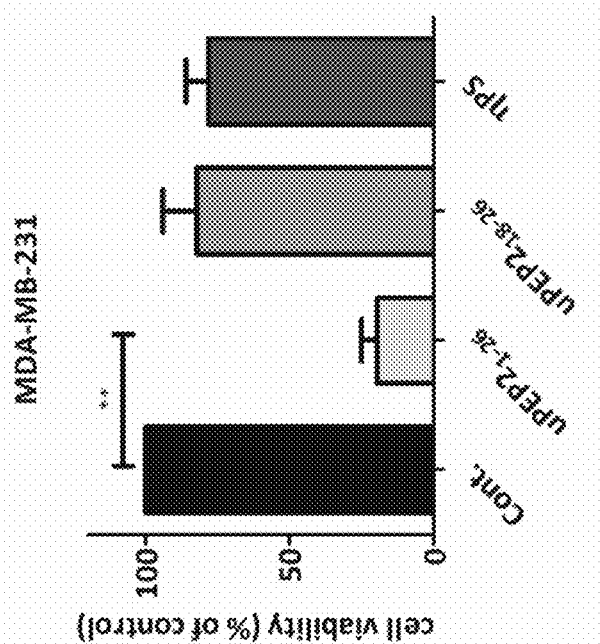
Figure 4D:
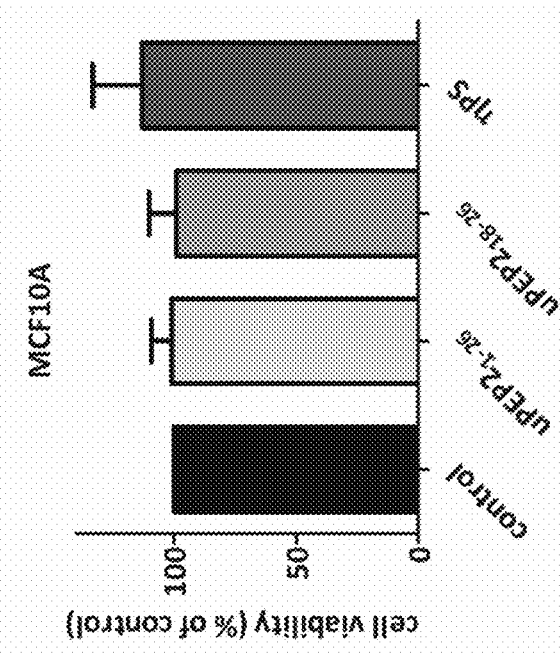

The nucleic and/or amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named 3278_1_3001_seq.txt, created Aug. 5, 2021, about 9 KB, which is incorporated by reference herein.

SEQ ID NO: 1 is the PKCeta derived uORF encoded peptide.

SEQ ID NO: 2 is the PKCeta derived uORF encoded peptide with the C-terminal addition of the CPP penetratin.

SEQ ID NO: 3 is the pseudosubstrate-containing fragment of the PKCeta derived uORF.

SEQ ID NO: 4 is the pseudosubstrate-containing fragment of the PKCeta derived uORF containing an alanine substitution at Cys-10.

SEQ ID NO: 5 is the full-length PKCeta derived uORF containing an alanine substitution at Cys-10.

SEQ ID NO: 6 is the pseudosubstrate-containing fragment of the PKCeta derived uORF containing a serine substitution at Ala-6.

SEQ ID NO: 7 is the pseudosubstrate-containing fragment of the PKCeta derived uORF containing a threonine substitution at Ala-6.

SEQ ID NO: 8 is the full-length PKCeta derived uORF containing a serine substitution at Ala-6.

SEQ ID NO: 9 is the full-length PKCeta derived uORF containing a threonine substitution at Ala-6.

SEQ ID NO: 10 is the CPP.

SEQ ID NO: 11 is the PKCzeta uORF.

SEQ ID NO: 12 is the PKCzeta uORF without the two C-terminal amino acids.

SEQ ID NO: 13 is a CPP arginine (R) repeat.

SEQ ID NOs: 14-18 are illustrative a nuclear localization signals (NLSs).

SEQ ID NO: 19 is the encoded peptide sequence of the pseudo-substrate sequence of novel PKCη isoform (ηPC).

SEQ ID NO: 20 is the Rhesus encoded peptide sequence of uORF2 from PKCη.

SEQ ID NO: 21 is the Elephant encoded peptide sequence of uORF2 from PKCη.

SEQ ID NO: 22 is the Dog encoded peptide sequence of uORF2 from PKCη.

SEQ ID NO: 23 is the Mouse encoded peptide sequence of uORF2 from PKCη.

SEQ ID NO: 24 is the Rat encoded peptide sequence of uORF2 from PKCη.

SEQ ID NO: 25 is the conventional PKCα internal pseudo-substrate sequence.

SEQ ID NO: 26 is the conventional PKCβ internal pseudo-substrate sequence.

SEQ ID NO: 27 is the conventional PKCγ internal pseudo-substrate sequence.

SEQ ID NO: 28 is the novel PKCδ internal pseudo-substrate sequence.

SEQ ID NO: 29 is the novel PKCΣ internal pseudo-substrate sequence.

SEQ ID NO: 30 is the atypical PKCζ internal pseudo-substrate sequence.

SEQ ID NO: 31 is the atypical PKCλ/ι internal pseudo-substrate sequence.

SEQ ID NO: 32 is the summary sequence of variant PKCeta derived uORF encoded peptide.

SEQ ID NOs: 33-35 are shRNA sequences for targeting PKCη expression.

DETAILED DESCRIPTION

I. Abbreviations

CPP cell penetrating peptide
PKC protein kinase C
PS pseudo substrate
uORF upstream open reading frame

II. Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example." In case of conflict, the present specification, including explanations of terms, will control. In addition, all the materials, methods, and examples are illustrative and not intended to be limiting.

Aberrant: Abnormal. As used herein, aberrant cell proliferation or cell division indicates overproliferation or hyperproliferation as might occur in a subject diagnosed with a cancer or hyperproliferative disease.

Administration: The introduction of a composition into a subject by a chosen route. Administration of an active compound or composition can be by any route known to one of skill in the art. Administration can be local or systemic. Examples of local administration include, but are not limited to, topical administration, subcutaneous administration, intramuscular administration, intrathecal administration, intrapericardial administration, intra-ocular administration, or topical ophthalmic administration In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs, such as vascular stents or other reservoirs, and delivery devices such as biodegradable implants, which release the active agents and compounds over extended time intervals for sustained and/or localized treatment effects.

Systemic administration includes any route of administration designed to distribute an active compound or composition widely throughout the body via the circulatory system. Thus, systemic administration includes, but is not limited to intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

Antagonist: A molecule or compound that tends to nullify the action of another, such as a phosphatase activity, or in some instances that blocks the ability of a given chemical to bind to its receptor or other interacting molecule, preventing a biological response. Antagonists are not limited to a specific type of compound, and may include in various embodiments peptides, antibodies and fragments thereof, and other organic or inorganic compounds (for example, peptidomimetics and small molecules). As used herein, "inhibitor" is synonymous with "antagonist".

Antisense inhibitor: Refers to an oligomeric compound that is at least partially complementary to the region of a target nucleic acid molecule to which it hybridizes. As used herein, an antisense inhibitor (also referred to as an "antisense compound") that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulation expression. Nonlimiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound.

Cancer: The product of neoplasia is a neoplasm (a tumor or cancer), which is an abnormal growth of tissue that results from excessive cell division. A tumor that does not metastasize is referred to as "benign." A tumor that invades the surrounding tissue and/or can metastasize is referred to as "malignant." Neoplasia is one example of a proliferative disorder. A "cancer cell" is a cell that is neoplastic, for example a cell or cell line isolated from a tumor.

Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers (such as small cell lung carcinoma and non-small cell lung carcinoma), ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma, astrocytoma, medulloblastoma, craniopharyogioma, ependymoma, pinealoma, hemangioblastoma, acoustic neuroma, oligodendroglioma, menangioma, neuroblastoma and retinoblastoma).

Cell Penetrating Peptide (CPP): A short polypeptide, typically less than or equal to 40 amino acids long, with the ability to translocate across the cell membrane and gain access to the cytoplasm, along with any molecule linked to the CPP. As used herein, CPPs are synonymous with and encompasses the peptides and sequences known in the art as "protein transduction domain (PTD)," "Trojan Protein," and "membrane translocating sequence (MTS)." Typical CPPs are positively charged, with amino acids such as arginine and lysine predominating in their sequence. Particular non-limiting examples of CPPs include polylysine or polyarginine peptides, for example but not limited to between 3 and 20 amino acids, penetratin, TAT, SynB1, SynB3, PTD-4, PTD-5, FHV-Coat (35-49), BMV Gag (7-25), HTLV-II Rex (4-16), D-Tat, R9-Tat, Transportan, MAP, SBP, NLS, FBP, MPG, Pep-1, and Pep-2.

Nuclear localization signal (NLS): The terms "nuclear localization signal" and "NLS" sequence as described herein are used interchangeably and refers to an amino acid sequence which is capable of inducing transport of molecules comprising such sequence(s) or linked to such sequences into the nucleus of cells. The NLS can, for example, direct transport of a protein with which it is associated from the cytoplasm of a cell across the nuclear envelope barrier. The NLS is intended to encompass not only the nuclear localization sequence of a particular peptide, but also derivatives thereof that are capable of directing translocation of a cytoplasmic polypeptide across the nuclear envelope barrier. NLSs are capable of directing nuclear translocation of a polypeptide when attached to the N-terminus, the C-terminus, or both the N- and C-termini of the polypeptide.

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating a breast cancer, an ovarian cancer, or another tumor, such as an anti-neoplastic agent. In one embodiment, a chemotherapeutic agent is a radioactive compound. One of skill in the art can readily identify a chemotherapeutic agent of use (see for example, Slapak and Kufe, *Principles of Cancer Therapy*). Non-limiting examples of chemotherapeutic agents include etoposide, cisplatin, paclitaxel, docetaxel, doxorubicin, epirubicin, topotecan, irinotecan, gemcitabine, iazofurine, gemcitabine, etoposide, vinorelbine, tamoxifen, valspodar, cyclophosphamide, methotrexate, fluorouracil, mitoxantrone and vinorelbine. Combination chemotherapy is the administration of more than one agent to treat cancer, including a combination of the peptides described herein and one or more chemotherapeutic agent for example, chemotherapy agents which target tumor DNA, for example inducing strand breaks or sequence errors.

Chemotherapeutic agents can be provided to a subject in various formulations and treatment regimens. In some embodiments, the chemotherapeutic agent can be provided in one or more formulations separate from other treatment agents described herein such as peptide or nucleic acid agents. In other embodiments the chemotherapeutic agent is linked or conjugated to the peptides and or nucleic acids described herein. Various methods are known in the art for linking molecules to peptides. One non-limiting example that is used is the introduction of a non-canonical amino acid to the peptide followed by a chemical reaction that attaches a molecule of interest to the R group of the incorporated non-canonical amino acid (see Kubyshkin et al, *Biotechnology Journal*, 3 Jul. 2017).

Chimera: A nucleic acid sequence, amino acid sequence, or protein that comprises nucleic acid sequence, amino acid sequence, or protein from two or more sources, for example amino acid sequence from two or more different species or two or more polypeptides from the same species. In general, chimeric sequences are the result of genetic engineering. The PKCeta uORF2-derived peptides fused to at least one CPP described herein are an example of a polypeptide chimera.

Contacting: Placement in direct physical association. Includes both in solid and liquid form. Contacting can occur in vitro with isolated cells or in vivo by administering to a subject.

Effective amount of a composition: A quantity of a composition, including the isolated peptides described herein, sufficient to achieve a desired effect in a subject being treated. An effective amount of a composition can be administered in a single dose, or in several doses, for example daily, during a course of treatment. However, the effective amount of the composition will be dependent on the composition applied, the subject being treated, the severity and type of the affliction, and the manner of administration of the composition.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof.

Expression Control Sequences: Nucleic acid sequences that regulate the expression of a heterologous nucleic acid sequence to which it is operatively linked, for example the expression of the described PKCeta uORF2-derived polypeptides can be operably linked to expression control sequences. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

Functional fragments and variants of a polypeptide: Included are those fragments and variants of the described PKCeta/PKCzeta uORF2-derived polypeptides that maintain one or more functions of the parent polypeptides. It is recognized that the gene or cDNA encoding a polypeptide can be considerably mutated without materially altering one or more the polypeptide's functions. First, the genetic code is well-known to be degenerate, and thus different codons encode the same amino acids. Second, even where an amino acid substitution is introduced, the mutation can be conservative and have no material impact on the essential functions of a protein. Third, part of a polypeptide chain can be deleted without impairing or eliminating all of its functions. Fourth, insertions or additions can be made in the polypeptide chain for example, adding epitope tags, without impairing or eliminating its functions Other modifications that can be made without materially impairing one or more functions of a polypeptide include, for example, in vivo or in vitro chemical and biochemical modifications or the incorporation of unusual amino acids. Such modifications include, for example, acetylation, carboxylation, myristoylation, phosphorylation, glycosylation, ubiquination, labeling, e.g., with radionucleides, and various enzymatic modifications, as will be readily appreciated by those well skilled in the art. A variety of methods for labeling polypeptides and labels useful for such purposes are well known in the art, and include radioactive isotopes such as $^{32}$P, ligands which bind to or are bound by labeled specific binding partners (e.g., antibodies), fluorophores, chemiluminescent agents, enzymes, and antiligands. Functional fragments and variants can be of varying length.

Heterologous: A type of sequence that is not normally (i.e. in the wild-type sequence) found adjacent to a second sequence. In one embodiment, the sequence is from a different genetic source, such as a virus or organism, than the second sequence. Chimeric polypeptides, such as those described herein are often composed of heterologous sequences.

Hyperproliferative disease: A disease or disorder characterized by the uncontrolled proliferation of cells. Hyperproliferative diseases include, but are not limited to malignant and non-malignant tumors and psoriasis, and can be treated by active agents (such as the PKCeta uORF2-derived peptides described herein) that can inhibit cellular proliferation.

Isolated: A biological component (such as a nucleic acid, protein or organelle) that has been substantially separated or purified away from other biological components in the cell of the organism in which the component naturally occurs, i.e., other chromosomal and extra-chromosomal DNA and RNA, proteins and organelles. Nucleic acids and proteins that have been isolated include nucleic acids and proteins purified by standard purification methods. The term also embraces nucleic acids and proteins prepared by recombinant expression in a host cell as well as chemically synthesized nucleic acids and proteins, such as the PKCeta uORF2-derived peptides described herein.

Neoplasia, malignancy, cancer and tumor: A neoplasm is an abnormal growth of tissue or cells that results from excessive cell division (cellular proliferation). Neoplastic growth can produce a tumor. The amount of a tumor in an individual is the "tumor burden" which can be measured as the number, volume, or weight of the tumor. A tumor that does not metastasize is referred to as "benign." A tumor that invades (or migrates into) the surrounding tissue and/or can metastasize is referred to as "malignant." Malignant tumors are also referred to as "cancer."

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers useful in this disclosure are conventional. *Remington's Pharmaceutical Sciences*, by Lloyd V. Allen, Jt. (ed.), 22nd Edition (2012) describes compositions and formulations suitable for pharmaceutical delivery of the compounds herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. Incubating includes exposing a target to an agent for a sufficient period of time for the agent to interact with a cell. Contacting includes incubating an agent in solid or in liquid form with a cell.

Protein Kinase C (PKC): Is a family of protein kinase enzymes understood to play key roles in cellular signal transduction cascades, and associated with mediating immune response, cell growth and regulation of cell division, and in learning and memory. The PKC family is divided into three subfamilies: conventional, novel and atypical. Each subfamily can be further divided into multiple isoforms. Particular examples of conventional isoforms include α, β and γ; novel isoforms include δ, ε and η; and atypical isoforms include ζ and λ/ι.

Polypeptide: A polymer in which the monomers are amino acid residues which are joined together through amide bonds. The term polypeptide, protein, or peptide, as used herein encompasses any amino acid sequence and includes modified sequences such as glycoproteins. The term polypeptide is specifically intended to cover naturally occurring proteins, as well as those that are recombinantly or synthetically produced.

The term polypeptide fragment refers to a portion of a polypeptide which exhibits at least one useful epitope. The phrase "functional fragments or variants of a polypeptide" refers to all fragments of a polypeptide that retain an activity, or a measurable portion of an activity, of the polypeptide from which the fragment is derived Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Preventing or treating a disease: Preventing a disease refers to inhibiting the full development of a disease, for example inhibiting the development of myocardial infarction in a person who has coronary artery disease or inhibiting the progression or metastasis of a tumor in a subject with a neoplasm. Treatment refers to a therapeutic intervention that ameliorates a sign or symptom of a disease or pathological condition after it has begun to develop.

Purified: The term purified does not require absolute purity; rather, it is intended as a relative term. Thus, for example, a purified protein preparation is one in which the protein referred to is more pure than the protein in its natural environment within a cell.

Radiation Therapy (Radiotherapy): The treatment of disease (e.g., cancer or another hyperproliferative disease or condition) by exposure of a subject or their tissue to a radioactive substance. Radiation therapy is the medical use of ionizing radiation as part of cancer treatment to control malignant cells. Radiotherapy may be used for curative or adjuvant cancer treatment. It is used as palliative treatment where cure is not possible and the aim is for local disease control or symptomatic relief.

Recombinant: A nucleic acid that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques. The expression vectors described herein that express a PKCeta uORF2-derived-peptide is an exemplary recombinant nucleic acid.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Methods of alignment of sequences for comparison are well known in the art, for example the NCBI Basic Local Alignment Search Tool (BLAST), which is available from several sources, for use in connection with the sequence analysis programs blastp, blastn, blastx, tblastn and tblastx. It can be accessed at the NCBI website, together with a description of how to determine sequence identity using this program.

Subject: Living multi-cellular organisms, including vertebrate organisms, a category that includes both human and non-human mammals.

Therapeutically effective amount: A quantity of compound sufficient to achieve a desired effect in a subject being treated. An effective amount of a compound may be administered in a single dose, or in several doses, for example daily, during a course of treatment. However, the effective amount will be dependent on the compound applied, the subject being treated, the severity and type of the affliction, and the manner of administration of the compound. For example, a therapeutically effective amount of an active ingredient can be measured as the concentration (moles per liter or molar-M) of the active ingredient (such as a small molecule, peptide, protein, or antibody) in blood (in vivo) or a buffer (in vitro) that produces an effect.

Vector: A nucleic acid molecule as introduced into a host cell, thereby producing a transfected host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

III. Overview of Several Embodiments

Provided herein are isolated, synthetic and chimeric, peptides derived from an uORF of the PKCeta isoform, and particularly an isolated polypeptide including an amino acid sequence at least 70% identical to the amino acid sequence set forth as SEQ ID NO: 32.

Further described herein, is the isolated polypeptide of SEQ ID NO: 32 wherein the amino acid at position 10 is alanine, as set forth herein as SEQ ID NO: 5. Additionally described herein, is the isolated polypeptide of SEQ ID NO:32 wherein the amino acid at position 10 is cysteine, as set forth herein as SEQ ID NO: 1.

In particular embodiments, the isolated polypeptide includes a peptide having an amino acid sequence of at least 70% identical to SEQ ID NOs: 5, 11, or 19.

In particular embodiments, the described isolated polypeptides include a myristoyl group.

In some embodiments, the described isolated polypeptides include at least one cell penetrating peptide (CPP), for example a penetratin CPP sequence. In a particular embodiment, described polypeptide is a chimeric amino acid sequence having the sequence set forth as SEQ ID NO: 2.

Additionally, described herein are nucleic acids encoding the provided isolated polypeptides. In particular embodiments, the polypeptide-encoding nucleic acids are part of and operably linked to an expression vector.

Further described herein are pharmaceutical compositions that include the described isolated polypeptides or nucleic acids and a pharmaceutically-acceptable carrier or excipient.

In some embodiments, the described isolated polypeptides or nucleic acids are used in the treatment of a disease or condition associated with aberrant cell proliferation, such as a disease or condition results in a benign abnormal cell growth or a benign tumor. In other examples, the disease or condition is a cancer. In a particular embodiment, such uses include the preparation of a medicament for treating the disease or condition associated with aberrant cell proliferation.

In some embodiments, the described isolated polypeptides or nucleic acids are administered together with a chemotherapy agent, surgery or radiotherapy (which itself can be administered in a separate formulation or conjugated to the described polypeptides or nucleic acids). In particular embodiments the chemotherapy agent is a DNA damaging agent. In further particular embodiments the DNA damaging chemotherapy agent is etoposide.

Also described are methods for treatment of a disease or condition associated with aberrant cell proliferation that include administering to a subject in need thereof a therapeutically effective amount of a described isolated peptide thereby treating the disease or condition. In some embodiments, the isolated peptide is provided to the subject as a nucleic acid capable of expressing the isolated peptide. In particular embodiments, the disease or condition results in benign abnormal cell growth or a benign tumor. In other embodiments, the disease is a cancer.

The provided methods of treatment also include methods of inhibiting cellular proliferation or cancer metastasis in a subject by administering to a subject in need thereof a therapeutically effective amount of a described isolated peptide and a chemotherapeutic agent (alone or conjugated to the described peptide); thereby inhibiting the cellular proliferation or cancer metastasis. Particular embodiments of such methods utilize a nucleic acid capable of expressing the isolated peptide.

IV. Protein Kinase C Peptide Inhibitors

Provided herein is the discovery that an upstream open reading frame (uORF) that was identified in the 5'-untranslated region (5'-UTR) of the protein kinase C (PKC) isoform eta encodes a 26-amino acid peptide that can inhibit PKC kinase activity, cellular migration, and cellular proliferation, particularly in cancer cells. Within this peptide, a 17 amino acid subpeptide was identified that contains homology to the PKC pseudosubstrate. Collectively, these peptides, and those described therefrom as referred to as PKCeta uORF-derived peptides.

Accordingly, described herein are isolated peptides of at least 17 amino acids which include an amino acid sequence at least 70% identical to the sequence set forth herein as SEQ ID NO: 3. The described isolated peptide, which can be produced synthetically, includes functional variants, as well as sequence variants of at least 17 amino acids that are at least 70-99% identical to SEQ ID NO: 3, including peptides that are at least 70%, 75%, 80%, 85%, 90%, 95%, 98% or more identical to SEQ ID NO: 3.

Particular embodiments of the described peptides include a peptide sequence at least 26 amino acids long, and has the amino acid sequence of the peptide produced by the PKCeta uORF2, and which is set forth herein as SEQ ID NO: 1. Particular embodiments of the described peptide include peptides at least 70-99% identical to SEQ ID NO: 1, including peptides that are at least 70%, 75%, 80%, 85%, 90%, 95%, 98% or more identical to SEQ ID NO: 1.

Particular embodiments of the described peptides include a peptide sequence at least 26 amino acids long which while similar to uPEP$_{1-26}$ (SEQ ID NO: 1) includes at least one alanine substitution, particularly at Cys-10. Particular embodiments of the described peptide include peptides at least 70-99% identical to SEQ ID NO: 5, including peptides that are at least 70%, 75%, 80%, 85%, 90%, 95%, 98% or more identical to SEQ ID NO: 5.

Also described herein is a sequence of the PKCeta-derived uORF encoded peptide set forth herein as SEQ ID NO: 32 (MASRGALRRXLSPGLPRLLHLSRGLA); wherein X is C (SEQ ID NO: 1) or A (SEQ ID NO: 5).

Further described herein is an isolated polypeptide at least 70%-99% identical to the peptide derived from the PKCzeta uORF and set forth herein as SEQ ID NO: 11, including peptides that are at least 70%, 75%, 80%, 85%, 90%, 95%, 98% or more identical to SEQ ID NO: 11.

Particular non-limiting embodiments of the described isolated synthetic polypeptides include polypeptides having sequences set forth herein as SEQ ID Nos 2, 4-9, and 12.

In particular embodiments, the described polypeptides, which can be synthetically produced or produced by way of an expression vector and purified from cell culture by standard means, are fused to at least one cell penetrating peptide (CPP), which can facilitate passage of an isolated polypeptide, such as a PKCeta uORF-derived peptide from the external environment and into the cellular interior. As described herein, numerous examples of CPPs exist, and which in fusion with a PKCeta uORF-derived peptide can be used to produce a chimeric PKCeta (or PKCzeta) uORF-derived peptide such as described herein. The PKCeta uORF-derived peptide chimeras can include one, two, three, or more CPPs from the same or multiple sources, which can be fused to a PKCeta uORF-derived peptide at the C- and/or N-terminus of the polypeptide. Particular examples of CPPs for use in the described chimeric peptides include the penetratin CPP (included herein as SEQ ID NO: 10) and the arginine repeats CPP (included herein as SEQ ID NO: 13), and which includes a poly-arginine sequence of 3-20 arginine residues. In some embodiments, the at least one CPP is fused directly to a PKCeta uORF-derived peptide and/or to other CPPs in the polypeptide chimera. In other embodiments, the at least one CPP is fused to a PKCeta uORF-derived peptide and/or to other CPPs in the polypeptide chimera by way of a peptide linker, which can be one or more amino acids linking the CPP(s) and/or PKCeta uORF-derived peptide.

In some embodiments, the CPP comprises arginine repeats as set forth in SEQ ID NO: 13 (RRRX), wherein R is arginine and X is an integer ranging from 0 to 17. In some embodiments, X is an integer ranging from 3 to 17, from 3 to 16, from 3 to 15, from 3 to 14, from 3 to 13, from 3 to 14, from 3 to 13, from 3 to 12, from 3 to 11, from 3 to 10, from 4 to 17, from 4 to 16, from 4 to 15, from 4 to 14, from 4 to 13, from 4 to 12, from 4 to 11, from 4 to 10, from 4 to 9, from 4 to 8, from 5 to 17, from 5 to 16, from 5 to 15, from 5 to 14, from 5 to 13, from 5 to 12, from 5 to 11, from 5 to 10, from 5 to 9, from 5 to 8, from 6 to 17, from 6 to 15, from 6 to 14, from 6 to 13, from 6 to 12, from 6 to 11, from 6 to 10, from 6 to 9, or from 6 to 8. Each possibility represents a separate embodiment of the present invention.

In some embodiments, peptides of the invention further comprise a nuclear localization (NLS) fused to the carboxy or amino terminus, wherein said NLS sequence comprises an amino acid sequence selected from the group consisting of: SEQ ID NO: 14 (KKKRR), SEQ ID NO: 15 (PKKKRRV), SEQ ID NO: 16 (KRRMKWKK), SEQ ID NO: 17 (KKKRK), and SEQ ID NO: 18 (KKKRK).

The described polypeptides can be produced by any method known to the art. In particular embodiments the polypeptides are chemically synthesized. In other embodiments, the polypeptides are produced by and purified from a suitable prokaryotic, fungal, plant, or animal cell host into which a suitable polypeptide-expression vector has been introduced. Methods of protein isolation and purification are also standard (e.g. methods of affinity chromatography, size exclusion chromatography and the like).

As indicated above, variants, fragments, and analogs of the described polypeptides are included in the current disclosure. Such polypeptides include polypeptides that share about 60%, 70%, 75%, 80%, 85%, 90%, 95%, or 98% sequence identity with the described PKCeta or PKCzeta uORF-derived peptides and chimeras. Other exemplary variants include peptides that differ by only one, two or three amino acids from those set forth herein. In particular embodiments, the variation from those sequences expressly described herein can be conservative substitutions that one of skill will not expect to significantly alter the shape or charge of the polypeptide.

The described polypeptides also include those polypeptides that share 100% sequence identity to those indicated, but which differ in post-translational or post-synthesis modifications from the native sequence. For example, the described synthetic polypeptides can be acetylated at the N- or C-terminal ends of the polypeptide. Other examples include conjugation of a palmitic acid group at either terminus of the peptide or other modifications common in the art of polypeptide synthesis such as myristoylation.

In particular embodiments, the described PKCeta or PKCzeta uORF-derived peptide, peptides and chimeric peptides are provided as a discrete biomolecule. In other embodiments, the described polypeptides are a domain of a larger polypeptide, such as an independently-folded structural domain, or an environment-accessible functional domain.

Also provided herein are nucleic acids encoding the described PKCeta or PKCzeta uORF-derived polypeptides and chimeric polypeptides, including variations due to codon degeneracy and particular nucleic acid sequences optimized for the codon bias of bacterial, animal, and plant cells.

In particular embodiments, the described nucleic acid sequences are contained within a DNA cloning and/or expression plasmid as are standard in the art. It will be appreciated that any standard expression plasmid can be used to express one or more of the described polypeptides and chimeric polypeptide-encoding nucleic acids, as discussed herein. Such plasmids will minimally contain an origin of replication, selection sequence (such as, but not limited to, an antibiotic resistance gene), and expression control sequences operably linked to the PKCeta or PKCzeta uORF-derived peptide or chimeric peptide-encoding nucleic acid. In particular embodiments, the expression plasmids include post-translational sequences (e.g. signal sequences to direct polypeptide processing and export) that are encoded in-frame with the PKCeta or PKCzeta uORF-derived polypeptides or chimeric polypeptide-encoding nucleic acids.

Particular non-limiting examples of bacterial expression plasmids include IPTG-inducible plasmids, arabinose-inducible plasmids and the like. Other non-limiting examples of expression induction include light induction, temperature induction, nutrient-induction, and autoinduction, and mammalian-specific DNA expression plasmids. Custom-made expression plasmids are commercially available from suppliers such as New England Biolabs (Ipswich, Mass.) and DNA 2.0 (Menlo Park, Calif.). In a particular embodiment, a PKCeta or PKCzeta uORF-derived polypeptide or chimeric polypeptide-expressing plasmid can be designed for specific localized induction in response to a local cellular micro environment, such as the local environment of a particular cancer type.

V. Compositions for Treatment of Diseases Associated with Aberrant Cellular Proliferation Additionally, provided herein are compositions including the described isolated PKCeta or PKCzeta uORF-derived polypeptides, chimeric polypeptides, and encoding nucleic acids, for use in for treatment or prevention of a disease or condition characterized by aberrant cellular proliferation. Exemplary uses include the preparation of a medicament for the described treatment or prevention, as well as methods of treatment by administering the described compositions in a therapeutically effective amount to a subject in need thereof.

In addition to the peptide (synthetic or produced in vivo by a transfected nucleic acid) agents for reducing expression and activity of PKCeta, also described herein are compositions and methods for treatment of diseases and/or conditions associated with aberrant cellular proliferation that utilize RNA-targeting methodologies, such as use of siRNA and shRNA agents. RNA therapeutic agents (including those set forth herein as SEQ ID NOs 33-35) can be provided by any standard means of the art of delivering nucleic acid agents to a therapeutic target. Non-limiting examples include lipid-based transfection agents, solid polymeric delivery systems, and other systemic and local delivery methods and formulations described herein.

Diseases and conditions characterized by aberrant cellular proliferation are most commonly associated with benign and cancerous neoplasia. In particular examples where the disease or condition is a cancer, the described peptides and methods of their use allow for treatment of cancers that are particularly associated with aberrant or dysregulated PKC (PKCeta or PKCzeta in particular) function. Such cancers include breast cancer, lung cancer, colon cancer, glioma, head and neck, ovarian, gastric cancer, and pancreatic cancer.

In some examples, the described PKCeta or PKCzeta uORF-derived polypeptides, chimeric polypeptides, and encoding nucleic acids, RNA-targeting agents (RNA interference (RNAi) agents) are used in methods of treating particular characteristic symptoms of a cellular proliferation disease. In a particular example, the described peptides or RNAi agents can be administered to a subject to inhibit cellular proliferation, thereby decreasing and/or preventing cancer cell or tumor growth. As described herein the described PKCeta uORF-derived peptide or RNAi agent can inhibit cellular migration, as is required for metastasis of a tumor in a subject. Accordingly, in addition to inhibiting proliferation, the described peptides can be used in compositions and methods for inhibiting or reducing metastasis of a cancer, thereby reducing or even eliminating the spread of a cancer beyond its originating tumor.

In addition to methods for inhibiting cell proliferation and metastasis, the described PKCeta uORF-derived polypeptides, chimeric polypeptides, and encoding nucleic acids, and RNAi agents can be used in methods for treating Cerebral infarction, Rheumatoid Arthritis, Alzheimer's Disease, and Pain. Likewise, the described PKCzeta uORF-derived polypeptides, chimeric polypeptides, and encoding nucleic acids can be used in methods for treating memory and learning disorders, chronic obstructive pulmonary disease, and Type-2 Diabetes.

In particular embodiments, the therapeutic compositions described herein can be supplied in any pharmaceutically acceptable composition. In such embodiments, one or more PKCeta or PKCzeta uORF-derived polypeptide or chimeric polypeptide-expressing nucleic and RNAi agents are provided in a pharmaceutical formulation having a therapeutically effective dose of each therapeutic agent, as described herein, and including standard pharmaceutically acceptable salts, excipients, fillers and the like.

Various delivery systems are known and can be used to administer polypeptides and nucleic acids as therapeutic agents. Such systems include, for example, encapsulation in liposomes, microparticles, microcapsules, recombinant cells capable of expressing the therapeutic molecule(s), construction of a therapeutic nucleic acid as part of a retroviral or other vector, and the like. Methods of introduction include, but are not limited to, intrathecal, intradermal, intramuscular, intraperitoneal (ip), intravenous (iv), subcutaneous, intranasal, epidural, and oral routes. The therapeutics may be formulated for administration by any convenient route, including, for example, infusion or bolus injection, topical, absorption through epithelial or mucocutaneous linings (e.g., oral mucosa, rectal and intestinal mucosa, and the like) ophthalmic, nasal, and transdermal, and may be administered together with other biologically active agents. Pulmonary administration can also be employed (e.g., by an inhaler or nebulizer), for instance using a formulation containing an aerosolizing agent.

In a specific embodiment, it may be desirable to administer the described pharmaceutical treatments by injection, catheter, suppository, or implant (e.g., implants formed from porous, non-porous, or gelatinous materials, including membranes, such as sialastic membranes or fibers), and the like. In another embodiment, therapeutic agents are delivered in a vesicle, in particular liposomes.

In particular embodiments, the described polypeptides and nucleic acids can be formulated for immediate release, whereby they are immediately accessible to the surrounding environment, thereby providing an effective amount of the active agent(s), upon administration to a subject, and until the administered dose is metabolized by the subject.

In yet another embodiment, the described polypeptides and nucleic acids can be formulated in a sustained release formulation or system. In such formulations, the therapeutic agents are provided for an extended duration of time, such as 1, 2, 3, 4 or more days, including 1-72 hours, 24-48 hours, 16-36 hours, 12-24 hours, and any length of time in between. In particular embodiments, sustained release formulations are immediately available upon administration, and provide an effective dosage of the therapeutic composition, and remain available at an effective dosage over an extended period of time. In other embodiments, the sustained release formulation is not immediately available within the subject and only becomes available, providing a therapeutically effective amount of the active compound(s), after the formulation is metabolized or degraded so as to release the active compound(s) into the surrounding environment. Illustrative non-limiting examples of sustained release formulations include hydrogels and nanoparticles (e.g., Raza et al., Pharmaceutics 10, 2018; and Rivzi et al., Saud Pharm. J. 26, 2018).

In one embodiment, a pump may be used. In another embodiment, the sustained released formulations include polymeric materials commonly used in the art, such as in implants, gels, capsules, and the like.

In particular embodiments, the described polypeptides and nucleic acids are formulated using methods well known to those with skill in the art. For instance, in some embodiments, the compounds are formulated with a pharmaceutically acceptable carrier. The term "pharmaceutically acceptable" means approved by a regulatory agency of the federal or a state government or listed in the U.S. Pharmacopoeia or other generally recognized pharmacopoeia world-wide for use in animals, and, more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable, or synthetic origin, such as peanut oil, soybean oil, mineral oil, sesame oil, and the like. Saline solutions, blood plasma medium, aqueous dextrose, and glycerol solutions can also be employed as liquid carriers, particularly for injectable solutions. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like.

Examples of pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The described compositions can, if desired, also contain minor amounts of wetting or emulsifying agents, or pH buffering agents. The described compositions can take the form of solutions, suspensions, emulsion, tablets, pills, capsules, powders, all in immediate and sustained-release formulations as understood in the art. The therapeutic can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like.

Therapeutic preparations will contain a therapeutically effective amount of at least one active ingredient, preferably in purified form, together with a suitable amount of carrier so as to provide proper administration to the patient. The formulation should suit the mode of administration.

The ingredients of the described formulations can be supplied either separately or mixed together in unit dosage form, for example, in solid, semi-solid and liquid dosage forms such as tablets, pills, powders, liquid solutions, or suspensions, or as a dry lyophilized powder or water free concentrate in a hermetically sealed container such as an ampoule or sachette indicating the quantity of active agent. Kits comprising the described PKCeta or PKCzeta uORF-derived polypeptide or chimeric polypeptides or encoding nucleic acids are accordingly also contemplated herein.

In particular embodiments of the described pharmaceutical compositions and methods of their use, the described PKCeta or PKCzeta uORF-derived polypeptide or chimeric polypeptides or encoding nucleic acid is administered to the subject as a polypeptide. In other embodiments, it is administered to the subject by way of an expression vector containing a described nucleic acid. It will be appreciated that in such embodiments, expression of the polypeptide can be constitutive or induced, as is well-known in the art. In some embodiments, inducible expression systems can allow for specific targeting of an area, such as a local tumor environment which contains an inducing signal.

In some embodiments, the described PKCeta or PKCzeta uORF-derived polypeptide or chimeric polypeptide, or encoding nucleic acid thereof, is administered to the subject in combination with other pharmaceutical agents for treatment of the disease or condition under treatment. For example, in methods for treating breast cancer the described polypeptides or nucleic acids can be combined with trastuzumab (Herceptin) therapy. In other embodiments of cancer therapy, the described peptides or nucleic acids can be combined with a DNA damaging chemotherapeutic agents. Non-limiting examples of such agents include cisplatin, doxorubicin, 5-fluorouracil, etoposide, and gemcitabine (see also Cheung-Ong et al., Chem and Biol. 20, 2013). In other examples of cancer treatment, the described compositions can be combined with surgery and/or radiation therapy. When provided as part of a treatment regimen or a method of treatment in combination with other therapies, the described PKCeta or PKCzeta uORF-derived polypeptide or chimeric polypeptide or encoding nucleic acids can be administered to the subject in sequence (prior to or following) or concurrently with the described compositions. Where applicable, in particular embodiments, combinations of active ingredients can be administered to a subject in a single or multiple formulations, and by single or multiple routes of administration.

In particular embodiments, the chemotherapeutic agent is provided as a separate molecule or formulation, along with the described peptides and nucleic acid agents. In other embodiments in which a chemotherapeutic agent is administered "with" the described peptide or nucleic acid therapeutic, the chemotherapeutic agent is conjugated to the peptide or nucleic acids. Methods of conjugation are known to the art. In particular non-limiting examples, the chemotherapeutic and peptide (or nucleic acid) components may be joined via a biologically-releasable bond, such as a selectively-cleavable linker or amino acid sequence. For example, peptide linkers that include a cleavage site for an enzyme are contemplated. Exemplary forms of such peptide linkers are those that are cleaved by urokinase, plasmin, thrombin, Factor IXa, Factor Xa, or a metalloproteinase, such as collagenase, gelatinase, or stromelysin. Additionally, any other linking/coupling agents and/or mechanisms known to those of skill in the art can be used to combine the therapeutic agents described herein, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof. In a particular embodiment, a non-canonical amino acid is incorporated into or at the end of the described peptide sequence. Modification of and reaction with the R group of such non-canonical amino acids with methodologies such as those described can be used to conjugate a chemotherapeutic agent to the described peptides.

The amount of each therapeutic agent for use in the described compositions and methods, and that will be effective, will depend on the nature of the disorder or condition to be treated, as well as the stage of the disorder or condition. Therapeutically effective amounts can be determined by standard clinical techniques. The precise dose to be employed in the therapeutic compositions will also depend on the route of administration for use with the composition, and should be decided according to the judgment of the health care practitioner and each patient's circumstances. The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the host undergoing therapy.

The therapeutic compounds and compositions of the present disclosure can be formulated or administered at about the same dose throughout a treatment period, in an escalating dose regimen, or in a loading-dose regime (e.g., in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. In some embodiments long-term treatment with the drug is contemplated.

The following examples are provided to illustrate certain particular features and/or embodiments. These examples should not be construed to limit the disclosure to the particular features or embodiments described.

EXAMPLES

Example 1: Methods

Peptides

Peptides were synthetically produced by GL Biochem. (China).

Immunoprecipitations and In Vitro Kinase Assays

Immunoprecipitations were performed by using pre-absorbed mAbs on protein A/G-agarose beads for 1 h at room temperature. Excess Abs was removed by 3 washes in cold phosphate buffered saline (PBS) and Ab-coated beads were incubated with cell lysates overnight at 4° C. Immune complexes were precipitated by centrifugation followed by extensive washing with RIPA buffer without SDS (10 mM Tris-HCl pH 8.0, 100 mM NaCl, 5 mM EGTA, 1% NP-40, 45 mM β-mercaptoethanol, and 50 mM NaF). Equally samples of immunoprecipitates were divided to Eppendorf tubes to kinase assay. Myelin-basic protein 5 µg (MBP, Sigma #M1891) as substrate and the indicated peptides (2 or 10 µM) were added. Kinase reaction mix was prepared: $MgCl_2$ 5 mM, HEPES 1M, $CaCl_2$ 300 µM, TRIS-HCl pH 7.4 20 mM, PMA 1 µM, phosphatydil-serin 40 µg/ml, 'cold' ATP and gamma-ATP 5 mM (PerkinElmer). All preparations were performed in ice 0-4° C. Eppendorf tubes containing 20 µl beads mixed with 100 µl kinase assay mix were incubated for 30 min in 30° C. The reaction was stopped with 25 µl Sample buffer*5 and 5 min denaturation in 95° C. followed by spin down. All samples were run on SDS-PAGE 10% and transferred to nitrocellulose membrane (Sigma-Aldrich, USA). Kinase activity was evaluated with exposing reagents. After detection of the phosphorylated substrate (p-MBP) the membranes were exposed to anti-HA (Biolegends #901513) as loading control.

Wound Healing Assay

MCF-7 and MDA-MB-231 cells were seeded in 24-well plates and grown to full confluency. Subsequently, media with low serum (2% to MCF-7 and 0.1% to MDA-MB-231) containing the peptides were added to the wells for 4 h. Then, a scratch was placed in the middle of the well with a sterile 200 µl pipette tip (Eppendorf). After washing once with PBS, the respective treatments were returned. Wells were photographed at total magnification of 4× with an IX70 Olympus Optical light microscope (Tokyo, Japan). 3 Images for each well were taken every 24 h.

Cell Viability Assays

Presto Blue Assay

MCF-7 and MDA-MB-231 cells were seeded at $2\times10^4$ cells/well in 48-well plates. After 24 h serum free-media containing the peptides was added to the wells for 4 h. Then, medium with serum was added and the plate was incubated for 24 h at incubator (5% $CO_2$ humidified atmosphere at 37° C.). Following incubation, the medium with tested peptide was gently aspirated from each well and 25 µL of Presto-Blue™ reagent (Thermo #A13261) was added to each well of the 48-well plate and incubated at 37° C. in 5% $CO_2$ for 15 min, as recommended. The absorbance was recorded at 570 nm and detected by 'Infinite M200 PRO' reader.

XTT Assays

Cells were seeded on 96-wells plate at a cell density of 20,000 cells/well and were grown for 48 hours. Cells were treated as indicated for 48 hours. A XTT (#20-300-1000, Biological Industries) reaction solution was prepared (containing the XTT and activation solutions) and added (50 µl/well) into cell medium for 2-4 hours at 37° C. The plate was immediately read in an ELISA plate reader at 450-500 nm. Background reading was performed at 630 nm, and the results calculated as the differences between the values.

Mouse Cell Transplantation Procedure

Mice were anesthetized with a solution of 10 ml/mg Ketamine and 1.17 ml/mg xylazine, in saline. Anesthesia was injected intraperitoneally (IP) after sterilizing the inoculation area of the mice with 70% ethanol solution. Using a 27-gauge needle, 4T1 control and shPKCη knockdown cells (transfected with SEQ ID NOs 33-35 or scrambled control (obtained from the ATCC) were injected a few millimeters from the nipple, underneath the skin (120,000 cells in 50 µl per mouse).

Analysis of Animals During Study:

Each week, mice were tested for tumors and the primary tumors were examined by caliper. After 10 weeks, mice were euthanized and examined for metastases in lung, liver and spleen, and samples were prepared for immuno staining.

Example 2: Identification and Characterization of a PKCeta uORF-Derived Kinase Inhibitor It was previously reported that the translation of the protein kinase C isoform PKCeta is in part regulated via two uORFs. Sequence alignment of the human and mammalian PKCeta uORF2 sequences surprisingly demonstrated sequence conservation within species (FIGS. 1A and 1B). The high conservation supports its potential functional role. Furthermore, it was found that uORF2 contains a sequence motif that resembles the PS motif of the PKCs, thus the similarity between the various PKCs PS sequences and uORF2, supports the presence of the PS motif in uORF2. (FIG. 1C).

To test the possibility that the translated uORF2 peptide can regulate the kinase activity of PKCs, the full-length human PKCeta uORF2 peptide was produced (also described herein as MA-26 and/or uPEP2$_{1-26}$, SEQ ID NO: 1). Peptides lacking the PS motif, uPEP$_{9-26}$ and uPEP$_{18-26}$, were used as controls (FIG. 2A). As can be seen in FIGS. 2B and 2C, uPEP$_{1-26}$ is the strongest inhibitor when compared to the control peptide uPEP$_{9-26}$ and to ηPS. The effect of uPEP2$_{1-26}$ on the kinase activity of PKC subfamilies were tested as described above. As shown in FIG. 2D, uPEP2 strongly inhibits the kinase activity of PKCs from the novel PKC subfamily.

The in vitro effect of PKCeta uORF2 on cancer cell migration was tested in vivo by a standard scratch test assay, as described above. The cells were treated with either uPEP$_{1-26}$, uPEP$_{9-26}$, uPEP$_{18-26}$ and ηPS after which a scratch to a dish of confluent breast cancer cell lines MCF7 (breast cancer), MDA-MB-231 (breast cancer) and MCF10A (non-transformed mammary cells). It was demonstrated that uPEP$_{1-26}$ inhibited migration of the breast cancer MCF7 and MDA-MB-231 but not of the non-transformed MCF10A (FIG. 3).

The in vitro effect of PKCeta uORF2 on cell lines MCF7, MDA-MB-231, U251 MG and MCF10A proliferation was similarly tested. Out of the various peptides, uPEP$_{1-26}$, uPEP$_{9-26}$, uPEP$_{18-26}$ and ηPS, it was observed that uPEP$_{1-26}$ inhibited cell proliferation the most in the transformed cell lines as opposed to the non-transformed cells MCF10A (FIG. 4).

Further sequence comparison of the 5' untranslated regions for several PKC variants revealed the presence of uORFs and sequences analogous to the PKCeta pseudosubstrate (FIG. 8A). The uORF of PKCzeta containing a PS motif was successfully sequenced as depicted in FIG. 8B (SEQ ID No. 11).

These results demonstrate the identification in the PKCeta uORF2 of a short sequence resembling the PKC pseudosubstrate (PS) sequence, uPEP$_{1-26}$. The PKC PS is part of the backbone of all PKC isoforms, and functions as an internal inhibitor for PKC kinase activity. Our results show that the uPEP$_{1-26}$ peptide is an efficient inhibitor of PKCs kinase activity. We also show that it inhibits cell proliferation and migration of breast cancer cells and cell proliferation of glioblastoma cells. Furthermore, we found a PS motif in a uORF of another PKC isoform, PKCzeta. Our studies show for the first time the presence of a functional signature motif in uORFs. Our study introduces uORFs as new players in protein networks regulation, thus adding a new layer to the complexity of protein control and signaling cascades that were not explored before.

Example 3: PKCeta Knockdown Inhibits Tumor Formation

Figure 7B:
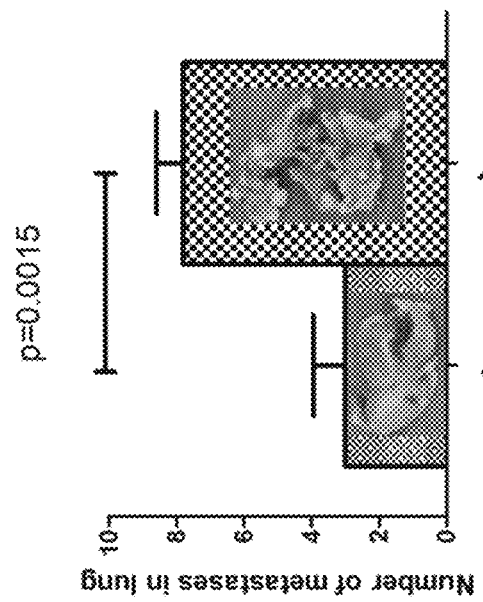
FIGS. 7A-7B show that PKCη-knockdown reduces tumor aggressiveness and metastasis formation in the breast 4T1 mouse model.
Figure 7A:
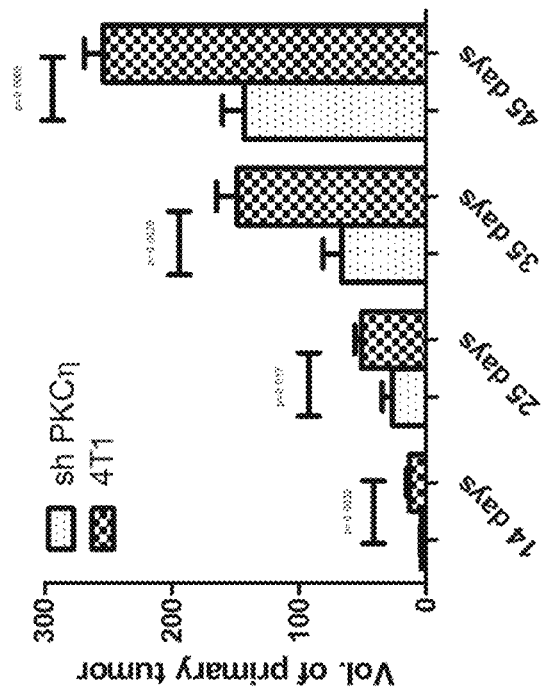

Example 2 demonstrated that inhibiting the activity of PKCeta has an inhibitory effect on the proliferation and migration of breast cancer cells. To test the in vivo effects of PKCeta on tumor formation, the establishment and growth of breast cancer cells with (4T1 control cells) and without PKCeta (PKCeta knockdown 4T1 cells) was compared. Comparison of tumor volume over time indicated a significant inhibition in tumor size in the PKCeta knockdown cells (FIG. 7A). PKCeta knockdown also inhibited the formation of tumor metastases (FIG. 7B). Results shown here are of the knockdown effect of expression of SEQ ID NO: 33, but similar results were observed using the shRNAs represented by those set forth herein as SEQ ID NOs 34 and 35. Together, these results indicate that inhibition of PKCeta, such as with the MA-26 or active subpeptides derived therefrom, can inhibit tumor growth and metastasis.

Figure 5:
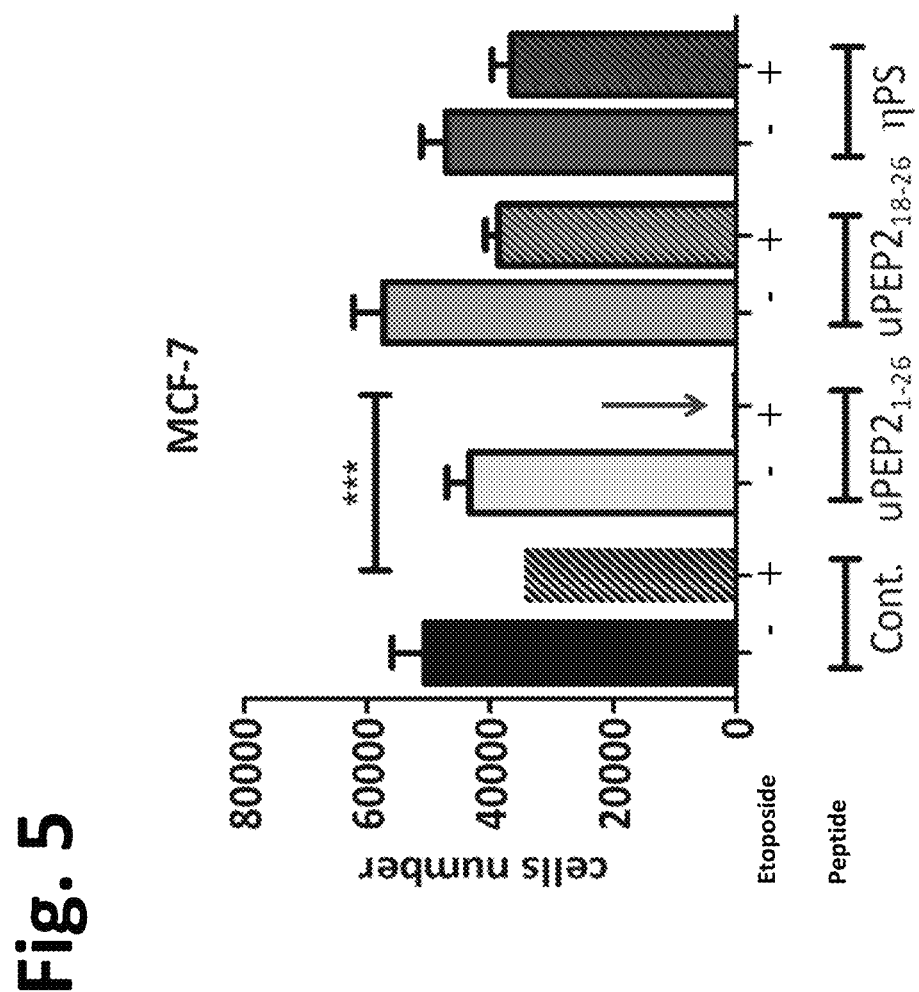
FIG. 5 shows a synergistic effect on the induction of cell death resulting from combining the peptide encoded by uORF2 (uPEP2$_{1-26}$) with etoposide. MCF-7 cells were seeded in 96 well plate for 24 hours. The indicated peptides (5 µM) were added for 4 hours. Then, etoposide (50 µM) was added to the wells for 48 hours. The plate was analyzed using XTT kit (Biological Industries, Israel) according to the manufacturer's instructions.

Example 4: Synergistic Effect of uPEP$_{1-26}$ and a Chemotherapy Agent in the Induction of Cell Death Breast cancer cell line, MCF-7, was treated with the indicated peptides (FIG. 5) with or without the DNA-targeting chemotherapy agent, Etoposide. When the cells were treated under conditions in which death by either etoposide or uPEP$_{1-26}$ resulted in only 10-30% cell death, the presence of both agents augmented cell death to about 95-100%, demonstrating synergism. Treatment with Etoposide alone induced some cell death, however, when Etoposide was administered together with uPEP$_{1-26}$, a synergistic effect was observed, resulting in apoptosis of nearly 100% as the cell (see FIG. 5, arrow). These results are strongly indicate the potential for a successful targeted dual cancer therapy.

Example 5: PKCeta uORF2 Peptide Mutant Effectively Reduces Cell Viability

Figure 6A:
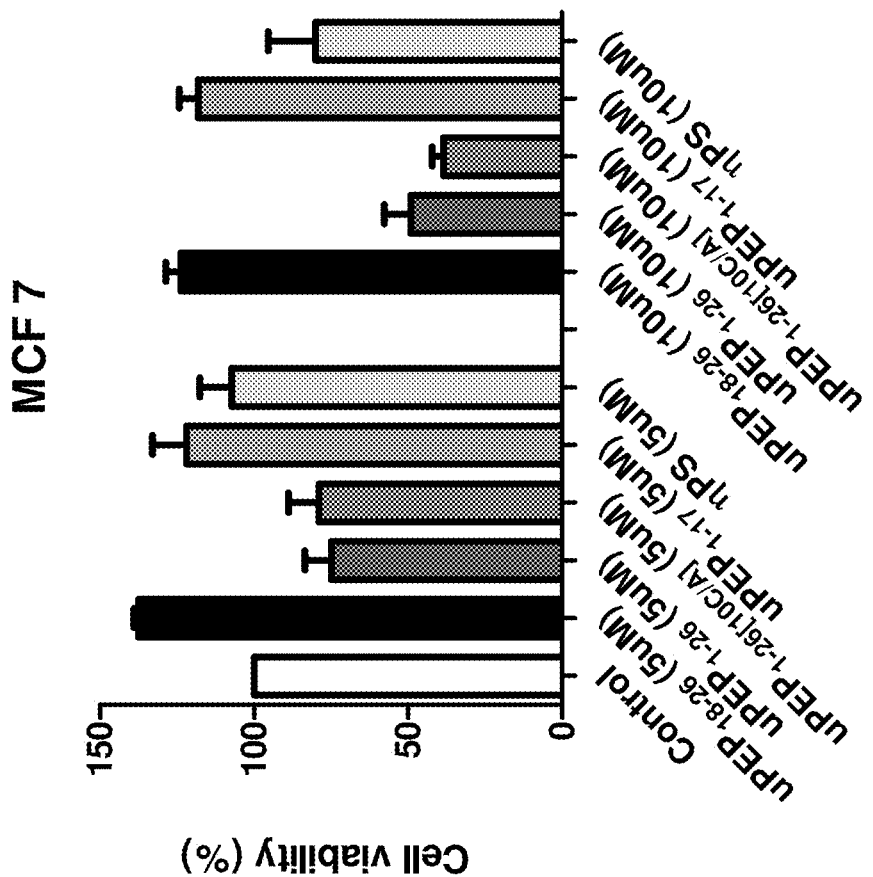
FIGS. 6A-6C show the efficacy of uORF2-encoded peptide mutated at position 10 (uPEP$_{1-26[c/a]}$) in reducing cell viability on various cell lines.
Figure 6B:
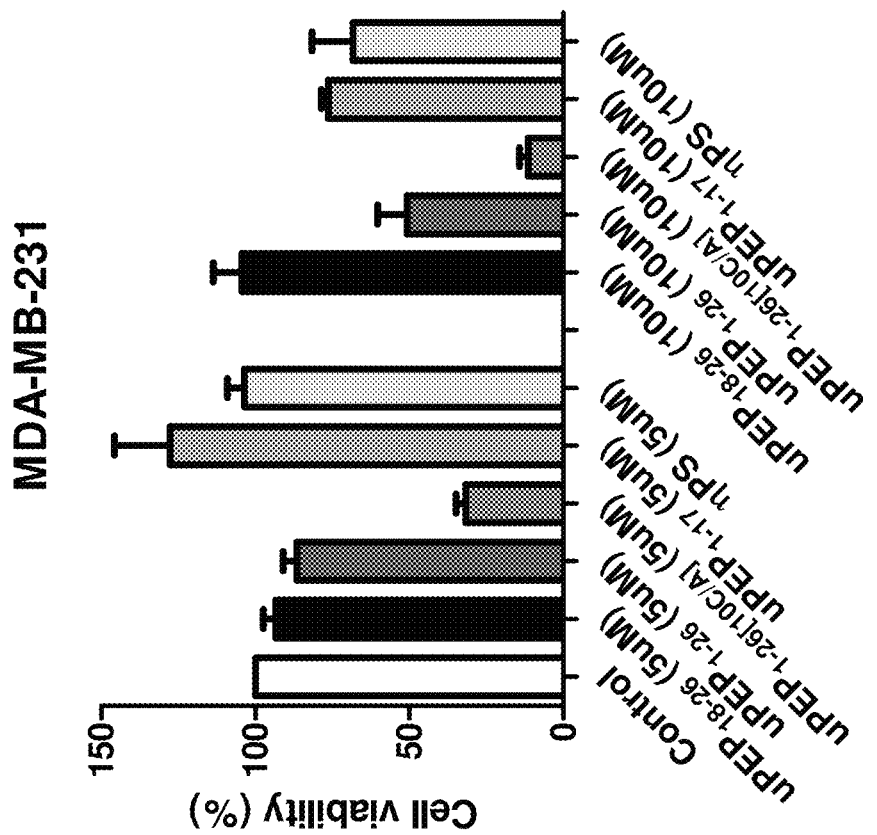
Figure 6C:
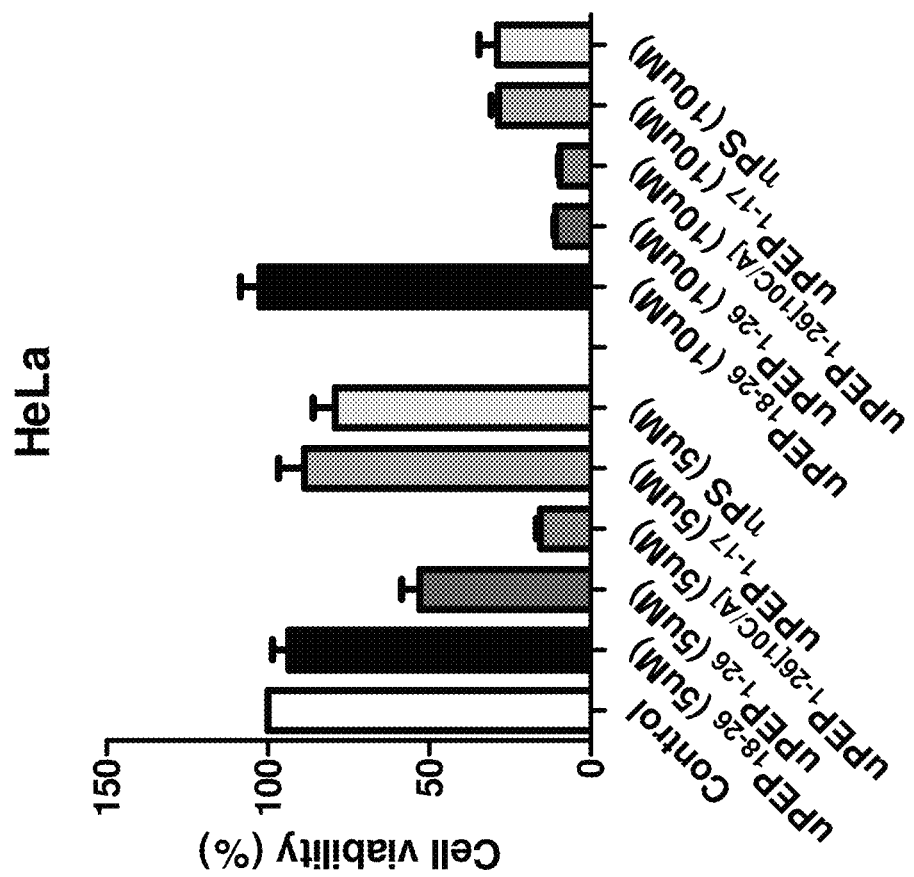

A uPEP2$_{1-26[10C/A]}$ mutation of the PKCeta uORF2 peptide (SEQ ID NO: 1) was synthesized containing an alanine substitution at Cys-10, herein referred to as SEQ ID No 5. Cell lines MCF-7 (FIG. 6A), MDA-MB-231 (FIG. 6B) and HeLa (FIG. 6C) were treated with uPEP2$_{18-26}$, uPEP2$_{1-26}$, uPEP2$_{1-26[10C/A]}$, uPEP2$_{1-17}$ and ηPS at doses of 5 μM and 10 μM in order to determine cell proliferation. As shown in the figures, the mutant uPEP$_{1-26[10C/A]}$ efficiently reduced cell viability compared to the other peptides.

Example 6: PKCeta uORF2 Peptide Mutants

Other mutants of the PKCeta uORF2 peptide (SEQ ID NO: 1) are synthesized and assayed for their activity in kinase, cell proliferation, and cell migration assays as described in Examples 1 and 2. Variants for assay include sequence variants set forth herein as SEQ ID NOs 2, 8 and 9. A myristoylated PKC uORF2 peptide is also assayed.

Also assayed is a 17-amino acid subpeptide fragment of SEQ ID NO: 1 which is restricted to the putative PKC pseudosubstrate (set forth herein as SEQ ID NO: 3), and variants thereof that are set forth herein as SEQ ID NOs 4, 6, and 7. The effects of C- or N-terminal added penetratin CPP (SEQ ID NO: 10) or myristoylation are also tested.

In vivo effects of the above peptides on cell proliferation, tumor growth, and metastasis are also tested.

Example 7: PKCzeta uORF Peptide

The sequence alignment discussed in Example 2 describes a putative uORF peptide in PKCzeta, also set forth herein as SEQ ID NO: 11. The kinase activity of this peptide and its variants, including the peptide listed as SEQ ID NO: 12 is tested as described above, as are the in vitro effects of this peptide on cell proliferation and migration, and its in vivo effects on tumor formation, memory, and learning.

We claim:

1. An isolated polypeptide comprising an amino acid sequence at least 95% identical to SEQ ID NO: 5, wherein the amino acid at position 10 is alanine.

2. The isolated polypeptide of claim 1, comprising the amino acid sequence of SEQ ID NO: 5.

3. The isolated polypeptide of claim 1, wherein the amino acid sequence comprises a myristoyl group.

4. The isolated polypeptide of claim 1, further comprising at least one cell penetrating peptide (CPP).

5. The isolated polypeptide of claim 4, wherein the CPP is penetratin.

6. A pharmaceutical composition comprising the isolated polypeptide of claim 1 and a pharmaceutically-acceptable carrier or excipient.

7. An isolated nucleic acid comprising a nucleic acid sequence encoding the isolated polypeptide of claim 1.

8. An expression vector comprising the isolated nucleic acid of claim 7.

9. A method for treatment of a disease or condition associated with aberrant cell proliferation, comprising:

administering to a subject in need thereof a therapeutically effective amount of the isolated peptide of claim 1, thereby treating the disease or condition.

10. The method of claim 9, wherein administering the isolated peptide is by providing to the subject a nucleic acid encoding the isolated peptide.

11. The method of claim 9, wherein the disease or condition results in benign abnormal cell growth or a benign tumor.

12. The method of claim 9, wherein the disease is a cancer.

13. A method of inhibiting cell proliferation and/or cancer metastasis in a subject, comprising:

administering to a subject in need thereof a therapeutically effective amount of the isolated peptide of claim 1, and optionally administering to the subject a chemotherapeutic agent;

thereby inhibiting the cell proliferation and/or cancer metastasis.

14. The method of claim 13, wherein administering the isolated peptide is by providing to the subject a nucleic acid encoding the isolated peptide.

* * * * *

SEQUENCE LISTING

<160> NUMBER OF SEQ ID NOS: 35

<210> SEQ ID NO 1
<211> LENGTH: 26
<212> TYPE: PRT
<213> ORGANISM: Homo sapiens

<400> SEQUENCE: 1

Met Ala Ser Arg Gly Ala Leu Arg Arg Cys Leu Ser Pro Gly Leu Pro
1               5                   10                  15

Arg Leu Leu His Leu Ser Arg Gly Leu Ala
            20                  25

<210> SEQ ID NO 2
<211> LENGTH: 33
<212> TYPE: PRT
<213> ORGANISM: Artificial Sequence
<220> FEATURE:
<223> OTHER INFORMATION: synthetic polypeptide

<400> SEQUENCE: 2

Met Ala Ser Arg Gly Ala Leu Arg Arg Cys Leu Ser Pro Gly Leu Pro
1               5                   10                  15

Arg Leu Leu His Leu Ser Arg Gly Leu Ala Arg Arg Met Lys Trp Lys
            20                  25                  30

Lys

<210> SEQ ID NO 3
<211> LENGTH: 17
<212> TYPE: PRT
<213> ORGANISM: Homo sapiens

<400> SEQUENCE: 3

Met Ala Ser Arg Gly Ala Leu Arg Arg Cys Leu Ser Pro Gly Leu Pro
1               5                   10                  15

Arg

<210> SEQ ID NO 4
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 4

Met Ala Ser Arg Gly Ala Leu Arg Arg Ala Leu Ser Pro Gly Leu Pro
1               5                   10                  15

Arg

<210> SEQ ID NO 5
<211> LENGTH: 26
<212> TYPE: PRT
<213> ORGANISM: Artificial Sequence
<220> FEATURE:
<223> OTHER INFORMATION: synthetic polypeptide

<400> SEQUENCE: 5

Met Ala Ser Arg Gly Ala Leu Arg Arg Ala Leu Ser Pro Gly Leu Pro
1               5                   10                  15

Arg Leu Leu His Leu Ser Arg Gly Leu Ala
            20                  25

```
<210> SEQ ID NO 6
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 6

Met Ala Ser Arg Gly Ser Leu Arg Arg Cys Leu Ser Pro Gly Leu Pro
1               5                   10                  15

Arg

<210> SEQ ID NO 7
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 7

Met Ala Ser Arg Gly Thr Leu Arg Arg Cys Leu Ser Pro Gly Leu Pro
1               5                   10                  15

Arg

<210> SEQ ID NO 8
<211> LENGTH: 26
<212> TYPE: PRT
<213> ORGANISM: Artificial Sequence
<220> FEATURE:
<223> OTHER INFORMATION: synthetic polypeptide

<400> SEQUENCE: 8

Met Ala Ser Arg Gly Ser Leu Arg Arg Cys Leu Ser Pro Gly Leu Pro
1               5                   10                  15

Arg Leu Leu His Leu Ser Arg Gly Leu Ala
            20                  25

<210> SEQ ID NO 9
<211> LENGTH: 26
<212> TYPE: PRT
<213> ORGANISM: Artificial Sequence
<220> FEATURE:
<223> OTHER INFORMATION: synthetic polypeptide

<400> SEQUENCE: 9

Met Ala Ser Arg Gly Thr Leu Arg Arg Cys Leu Ser Pro Gly Leu Pro
1               5                   10                  15

Arg Leu Leu His Leu Ser Arg Gly Leu Ala
            20                  25

<210> SEQ ID NO 10
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 10

Arg Arg Met Lys Trp Lys Lys
1               5

<210> SEQ ID NO 11
<211> LENGTH: 18
<212> TYPE: PRT
<213> ORGANISM: Homo sapiens
```

```
<400> SEQUENCE: 11

Met Gly Pro Arg Glu Ala Arg Leu Gln Val His Gln Leu Gln Thr Ala
1               5                   10                  15

Gly Pro

<210> SEQ ID NO 12
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 12

Met Gly Pro Arg Glu Ala Arg Leu Gln Val His Gln Leu Gln Thr Ala
1               5                   10                  15

<210> SEQ ID NO 13
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: X is Rn, wherein n=0 to 17

<400> SEQUENCE: 13

Arg Arg Arg Xaa
1

<210> SEQ ID NO 14
<211> LENGTH: 5
<212> TYPE: PRT
<213> ORGANISM: Homo sapiens

<400> SEQUENCE: 14

Lys Lys Lys Arg Arg
1               5

<210> SEQ ID NO 15
<211> LENGTH: 7
<212> TYPE: PRT
<213> ORGANISM: Homo sapiens

<400> SEQUENCE: 15

Pro Lys Lys Lys Arg Arg Val
1               5

<210> SEQ ID NO 16
<211> LENGTH: 8
<212> TYPE: PRT
<213> ORGANISM: Homo sapiens

<400> SEQUENCE: 16

Lys Arg Arg Met Lys Trp Lys Lys
1               5

<210> SEQ ID NO 17
<211> LENGTH: 5
<212> TYPE: PRT
<213> ORGANISM: Homo sapiens

<400> SEQUENCE: 17
```

Lys Lys Lys Arg Lys
1               5

<210> SEQ ID NO 18
<211> LENGTH: 5
<212> TYPE: PRT
<213> ORGANISM: Homo sapiens

<400> SEQUENCE: 18

Lys Lys Lys Arg Lys
1               5

<210> SEQ ID NO 19
<211> LENGTH: 17
<212> TYPE: PRT
<213> ORGANISM: Homo sapiens

<400> SEQUENCE: 19

Thr Arg Lys Arg Gln Arg Ala Met Arg Arg Val His His Gln Ile
1               5                   10                  15

Asn

<210> SEQ ID NO 20
<211> LENGTH: 26
<212> TYPE: PRT
<213> ORGANISM: Macaca mulatta

<400> SEQUENCE: 20

Met Ala Ser Arg Gly Ala Leu Gly Arg Cys Leu Ser Pro Gly Leu Pro
1               5                   10                  15

Arg Leu Leu Gln Leu Ser Arg Gly Leu Ala
            20                  25

<210> SEQ ID NO 21
<211> LENGTH: 26
<212> TYPE: PRT
<213> ORGANISM: Elephas maximus

<400> SEQUENCE: 21

Met Ala Gly Arg Gly Gly Leu Gly Arg Cys Phe Ser Pro Glu Leu Pro
1               5                   10                  15

Pro Leu Leu Arg Leu Pro Arg Gly Leu Ala
            20                  25

<210> SEQ ID NO 22
<211> LENGTH: 26
<212> TYPE: PRT
<213> ORGANISM: Canis familiaris

<400> SEQUENCE: 22

Met Thr Ser Gly Gly Gly Leu Gly Arg Cys Phe Ser Pro Glu Leu Arg
1               5                   10                  15

Pro Leu Arg Arg Leu Pro Arg Gly Leu Ala
            20                  25

<210> SEQ ID NO 23
<211> LENGTH: 26
<212> TYPE: PRT
<213> ORGANISM: Mus musculus

<400> SEQUENCE: 23

Met Ala Gly Arg Arg Gly Leu Gly Arg Cys Phe Phe Pro Glu Leu Pro
1               5                   10                  15

Pro Arg Pro Trp Gln Arg Arg Gly Leu Pro
            20                  25

<210> SEQ ID NO 24
<211> LENGTH: 26
<212> TYPE: PRT
<213> ORGANISM: Rattus rattus

<400> SEQUENCE: 24

Met Ala Gly Arg Arg Gly Leu Gly Cys Cys Phe Ser Arg Glu Leu Pro
1               5                   10                  15

Pro Arg Ala Trp Leu Arg Arg Gly Leu Pro
            20                  25

<210> SEQ ID NO 25
<211> LENGTH: 18
<212> TYPE: PRT
<213> ORGANISM: Homo sapiens

<400> SEQUENCE: 25

Arg Phe Ala Arg Lys Gly Ala Leu Arg Gln Lys Asn Val His Glu Val
1               5                   10                  15

Lys Asp

<210> SEQ ID NO 26
<211> LENGTH: 18
<212> TYPE: PRT
<213> ORGANISM: Homo sapiens

<400> SEQUENCE: 26

Arg Phe Ala Arg Lys Gly Ala Leu Arg Gln Lys Asn Val His Glu Val
1               5                   10                  15

Lys Asn

<210> SEQ ID NO 27
<211> LENGTH: 18
<212> TYPE: PRT
<213> ORGANISM: Homo sapiens

<400> SEQUENCE: 27

Leu Phe Cys Arg Lys Gly Ala Leu Arg Gln Lys Val Val His Glu Val
1               5                   10                  15

Lys Ser

<210> SEQ ID NO 28
<211> LENGTH: 18
<212> TYPE: PRT
<213> ORGANISM: Homo sapiens

<400> SEQUENCE: 28

Thr Met Asn Arg Arg Gly Ala Ile Lys Gln Ala Lys Ile His Tyr Ile
1               5                   10                  15

Lys Asn

<210> SEQ ID NO 29
<211> LENGTH: 17
<212> TYPE: PRT
<213> ORGANISM: Homo sapiens

<400> SEQUENCE: 29

Pro Arg Lys Arg Gln Gly Ala Val Arg Arg Arg Val His His Gln Val

<210> SEQ ID NO 30
<211> LENGTH: 17
<212> TYPE: PRT
<213> ORGANISM: Homo sapiens

<400> SEQUENCE: 30

Ser Ile Tyr Arg Arg Gly Ala Arg Arg Trp Arg Lys Leu Tyr Arg Ala
1               5                   10                  15
Asn

<210> SEQ ID NO 31
<211> LENGTH: 17
<212> TYPE: PRT
<213> ORGANISM: Homo sapiens

<400> SEQUENCE: 31

His Gln Arg Arg Gly Ala Ile Lys Gln Ala Lys Val His His Val Lys
1               5                   10                  15
Cys

<210> SEQ ID NO 32
<211> LENGTH: 26
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (10)..(10)
<223> OTHER INFORMATION: X is C or A

<400> SEQUENCE: 32

Met Ala Ser Arg Gly Ala Leu Arg Arg Xaa Leu Ser Pro Gly Leu Pro
1               5                   10                  15
Arg Leu Leu His Leu Ser Arg Gly Leu Ala
            20                  25

<210> SEQ ID NO 33
<211> LENGTH: 61
<212> TYPE: DNA
<213> ORGANISM: Artificial Sequence
<220> FEATURE:
<223> OTHER INFORMATION: synthetic polynucleotide

<400> SEQUENCE: 33
gatccccggc cgtcttaac tccgattgat ctcgatcaat cggagttaag acgggttttt   60
g                                                                   61

<210> SEQ ID NO 34
<211> LENGTH: 75
<212> TYPE: DNA
<213> ORGANISM: Artificial Sequence
<220> FEATURE:
<223> OTHER INFORMATION: synthetic polynucleotide

<400> SEQUENCE: 34
gatccccggg ggtctccaac ccggaaatat ctccttcctg tcagagagat atttccgggt   60
tggagaccct ttttg                                                    75

```
<210> SEQ ID NO 35
<211> LENGTH: 69
<212> TYPE: DNA
<213> ORGANISM: Artificial Sequence
<220> FEATURE:
<223> OTHER INFORMATION: synthetic polynucleotide

<400> SEQUENCE: 35
gatccccggc catcaagtga acggacataa cttcctgtca gattatgtcc gttcacttga      60
tggtttttg                                                              69
```